(12) United States Patent
Clancy et al.

(10) Patent No.: US 10,363,407 B2
(45) Date of Patent: Jul. 30, 2019

(54) PLUNGER-DRIVEN COLLET HANDLE AND SYSTEM FOR FIDUCIAL DEPLOYMENT

(71) Applicant: Cook Medical Technologies LLC, Bloomington, IN (US)

(72) Inventors: Michael Clancy, Limerick (IE); Darach McGrath, Tipperary County (IE); Triona Campbell, Clare County (IE); Patrick Mulcahy, Tipperary County (IE); Fionan Keady, Galway County (IE); Ciaran Toomey, Cork County (IE)

(73) Assignee: Cook Medical Technologies LLC, Bloomington, IN (US)

( * ) Notice: Subject to any disclaimer, the term of this patent is extended or adjusted under 35 U.S.C. 154(b) by 723 days.

(21) Appl. No.: 14/712,559

(22) Filed: May 14, 2015

(65) Prior Publication Data

US 2015/0360019 A1 Dec. 17, 2015

Related U.S. Application Data

(60) Provisional application No. 62/012,789, filed on Jun. 16, 2014.

(51) Int. Cl.
*A61M 37/00* (2006.01)
*A61B 90/00* (2016.01)
*A61B 17/34* (2006.01)

(52) U.S. Cl.
CPC ......... *A61M 37/0069* (2013.01); *A61B 90/39* (2016.02); *A61B 17/3468* (2013.01);
(Continued)

(58) Field of Classification Search
CPC ...... A61M 37/0069; A61M 2005/3125; A61M 2005/3126; A61M 31/007;
(Continued)

(56) References Cited

U.S. PATENT DOCUMENTS 2,009,393 A 7/1936 Failla
2,239,963 A 4/1941 Hoffert
(Continued)

FOREIGN PATENT DOCUMENTS

EP 0 093 101 A2 11/1983
EP 1 518 549 A1 3/2005
(Continued)

OTHER PUBLICATIONS

Ammar et al., "Fiducial placement for stereotactic radiation by using EUS feasibility when using a marker compatible with a standard 22-gauge needle," Gastrointestinal Endoscopy, vol. 71, No. 3, pp. 630-633, www.giejournal.org, St. Louis, MO 20210.
(Continued)

*Primary Examiner* — Kami A Bosworth
*Assistant Examiner* — Alexandra Lalonde
(74) *Attorney, Agent, or Firm* — Brinks Gilson & Lione

(57) ABSTRACT

Embodiments include a fiducial deployment system with a handle configured for actuation of the same, the handle including a collet mechanism actuatable for controlled, one-at-a-time deployment of fiducials. A fiducial may include one or more protuberances configured to engage one or more slots in a needle of the system. The needle may be configured to deliver a plurality of fiducials to a target location in serial fashion, one at a time. In certain embodiments, echogenic placement of fiducials may present certain advantages. The handle includes an actuation mechanism with a collet and plunger actuation member configured for incrementally or otherwise controlledly deploy one or more fiducials at a time by advancing a sty let through and/or retracting the body of a slotted needle in which fiducials are disposed with a fiducial protrusion extending into the needle slot, which also includes retaining structures that do not impede the needle lumen.

18 Claims, 11 Drawing Sheets

(52) U.S. Cl.
CPC . *A61B 2090/034* (2016.02); *A61B 2090/0804* (2016.02); *A61B 2090/0807* (2016.02); *A61B 2090/0811* (2016.02); *A61B 2090/3925* (2016.02); *A61B 2090/3987* (2016.02); *A61B 2560/0266* (2013.01)

(58) Field of Classification Search
CPC ........ A61M 2205/583; A61M 5/31568; A61M 5/31583; A61F 9/0008; A61F 9/0017; A61F 9/0026; A61B 90/39; A61B 2090/3904; A61B 2090/3987; A61B 2090/034; A61B 2090/0804; A61B 2090/0807; A61B 17/3468
See application file for complete search history.

(56) References Cited

U.S. PATENT DOCUMENTS

| | | |
|---|---|---|
| 2,269,963 A | 1/1942 | Wappler |
| 2,620,796 A | 12/1952 | Eriksen et al. |
| 3,470,834 A | 10/1969 | Bone |
| 3,815,798 A | 6/1974 | Lavitch et al. |
| 3,820,545 A | 6/1974 | Jefferts |
| 4,086,914 A | 5/1978 | Moore |
| 4,105,030 A | 8/1978 | Kercso |
| 4,154,239 A | 5/1979 | Turley |
| 4,451,254 A | 5/1984 | Dinius et al. |
| 4,646,740 A | 3/1987 | Peters et al. |
| 4,648,542 A | 3/1987 | Fox et al. |
| 4,661,103 A | 4/1987 | Harman |
| 4,700,692 A | 10/1987 | Baumgartner |
| 4,716,901 A | 1/1988 | Jackson et al. |
| 4,807,628 A | 2/1989 | Peters et al. |
| 4,976,686 A | 12/1990 | Ball et al. |
| 5,002,548 A | 3/1991 | Campbell et al. |
| 5,024,727 A | 6/1991 | Campbell et al. |
| 5,047,038 A | 9/1991 | Peters et al. |
| 5,281,197 A | 1/1994 | Arias et al. |
| 5,669,543 A | 9/1997 | Ueno |
| 5,755,726 A | 5/1998 | Pratt et al. |
| 5,810,769 A | 9/1998 | Schlegel et al. |
| 5,860,909 A | 1/1999 | Mich et al. |
| 6,004,320 A | 12/1999 | Casscells et al. |
| 6,186,144 B1 | 2/2001 | Davis et al. |
| 6,210,315 B1 | 4/2001 | Andrews et al. |
| 6,220,248 B1 | 4/2001 | Voegele et al. |
| 6,221,003 B1 | 4/2001 | Sierocuk et al. |
| 6,228,055 B1 | 5/2001 | Foerster et al. |
| 6,264,599 B1 | 7/2001 | Slater et al. |
| 6,267,718 B1 | 7/2001 | Vitali et al. |
| 6,283,948 B1 | 9/2001 | McKernan et al. |
| 6,347,241 B2 | 2/2002 | Burbank et al. |
| 6,402,677 B1 | 6/2002 | Jacobs |
| 6,432,035 B1 | 8/2002 | Ravins et al. |
| 6,450,938 B1 | 9/2002 | Miller |
| 6,569,077 B2 | 5/2003 | Schmidt |
| 6,592,508 B1 | 7/2003 | Ravins et al. |
| 6,613,002 B1 | 9/2003 | Clark et al. |
| 6,796,935 B1 | 9/2004 | Savino |
| 6,824,507 B2 | 11/2004 | Miller |
| 6,837,844 B1 | 1/2005 | Ellard et al. |
| 6,889,833 B2 | 5/2005 | Seiler et al. |
| 7,001,341 B2 | 2/2006 | Gellman et al. |
| 7,008,368 B2 | 3/2006 | Terwilliger et al. |
| 7,041,048 B2 | 5/2006 | Drobnik et al. |
| 7,083,566 B2 | 8/2006 | Tornes et al. |
| 7,104,945 B2 | 9/2006 | Miller |
| 7,144,386 B2 | 12/2006 | Korkor et al. |
| 7,214,206 B2 | 5/2007 | Rue et al. |
| 7,247,160 B2 | 7/2007 | Seiler et al. |
| 7,280,865 B2 | 10/2007 | Adler |
| 7,335,155 B2 | 2/2008 | Chu |
| 7,361,135 B2 | 4/2008 | Drobnik et al. |
| 7,407,054 B2 | 8/2008 | Seiler et al. |
| 7,429,240 B2 | 9/2008 | Miller |
| 7,465,279 B2 | 12/2008 | Beckman et al. |
| 7,510,549 B2 | 3/2009 | Rue et al. |
| 7,565,191 B2 | 7/2009 | Burbank et al. |
| 7,577,473 B2 | 8/2009 | Davis et al. |
| 7,588,528 B2 | 9/2009 | Drobnik et al. |
| 7,615,076 B2 | 11/2009 | Cauthen, II et al. |
| 7,651,505 B2 | 1/2010 | Lubock et al. |
| 7,736,343 B2 | 6/2010 | Marshall et al. |
| 7,819,820 B2 | 10/2010 | Field et al. |
| 7,850,639 B2 | 12/2010 | Rue et al. |
| 2003/0120141 A1 | 6/2003 | Adler |
| 2003/0233101 A1 | 12/2003 | Lubock et al. |
| 2003/0233126 A1 | 12/2003 | Kaplan et al. |
| 2004/0097780 A1 | 5/2004 | Otsuka |
| 2004/0236213 A1 | 11/2004 | Jones et al. |
| 2004/0260199 A1 | 12/2004 | Hardin, Jr. et al. |
| 2005/0038355 A1 | 2/2005 | Gellman et al. |
| 2005/0267319 A1 | 12/2005 | White et al. |
| 2006/0058569 A1 | 3/2006 | Chu |
| 2006/0173236 A1 | 8/2006 | White et al. |
| 2006/0235298 A1 | 10/2006 | Kotmel et al. |
| 2007/0093726 A1 | 4/2007 | Leopold et al. |
| 2007/0167736 A1 | 7/2007 | Dietz et al. |
| 2007/0270640 A1 | 11/2007 | Dimitriou et al. |
| 2008/0033280 A1 | 2/2008 | Lubock et al. |
| 2008/0033286 A1 | 2/2008 | Whitmore et al. |
| 2008/0243148 A1 | 10/2008 | Mikkaichi et al. |
| 2008/0249466 A1* | 10/2008 | Aubert ................ A61M 31/007 604/117 |
| 2008/0269688 A1 | 10/2008 | Colucci et al. |
| 2008/0287782 A1 | 11/2008 | Traboulsi et al. |
| 2009/0018439 A1 | 1/2009 | Jones et al. |
| 2009/0105518 A1 | 4/2009 | Schreiber et al. |
| 2009/0105584 A1 | 4/2009 | Jones |
| 2009/0131734 A1 | 5/2009 | Neustadter et al. |
| 2009/0209804 A1 | 8/2009 | Seiler et al. |
| 2009/0209903 A1* | 8/2009 | Cherif-Cheikh ........................... A61M 37/0069 604/63 |
| 2009/0227893 A1 | 9/2009 | Coonahan et al. |
| 2010/0010342 A1 | 1/2010 | Burbank et al. |
| 2010/0036241 A1 | 2/2010 | Mayse et al. |
| 2010/0042041 A1 | 2/2010 | Tune et al. |
| 2010/0063392 A1 | 3/2010 | Nishina et al. |
| 2010/0137891 A1 | 6/2010 | Shalon et al. |
| 2010/0280367 A1 | 11/2010 | Ducharme et al. |
| 2010/0331677 A1 | 12/2010 | Hong et al. |
| 2011/0028831 A1 | 2/2011 | Kent |
| 2011/0071424 A1 | 3/2011 | Nock et al. |
| 2011/0152611 A1 | 6/2011 | Ducharme et al. |
| 2011/0288581 A1 | 11/2011 | Paul, Jr. et al. |
| 2012/0265042 A1 | 10/2012 | Neinast et al. |
| 2013/0006101 A1 | 1/2013 | McHugo et al. |
| 2013/0006286 A1 | 1/2013 | Lavelle et al. |
| 2013/0096427 A1 | 4/2013 | Murray et al. |
| 2014/0121677 A1 | 5/2014 | Clancy et al. |
| 2016/0051766 A1* | 2/2016 | Marsh .................... A61M 5/20 604/207 |

FOREIGN PATENT DOCUMENTS

| | | |
|---|---|---|
| EP | 2 719 355 A2 | 4/2014 |
| FR | 2 762 517 A1 | 4/1997 |
| JP | 6323312 | 11/1994 |
| WO | WO 97/19724 A1 | 6/1997 |
| WO | WO 01/00101 A1 | 1/2001 |
| WO | WO 2007/094001 A2 | 8/2007 |
| WO | WO 2007/103204 A2 | 9/2007 |
| WO | WO 2008/016551 A1 | 2/2008 |
| WO | WO 2009/100106 A1 | 8/2009 |
| WO | WO 2009/132349 A2 | 10/2009 |
| WO | WO 2010/126750 A2 | 11/2010 |

(56) References Cited

FOREIGN PATENT DOCUMENTS

WO     WO 2012/152666 A1    11/2012
WO     WO 2014/133777 A1     9/2014

OTHER PUBLICATIONS

Classen et al. "Gastroenterological Endoscopy," EUS-Guided Implantation of Radiopaque Markers (Fiducials), p. 475.
DiMaio et al., "EUS-guided fiducial placement for image-guided radiation therapy in GI malignancies by using a 22-gauge needle (with videos)," Gastrointestinal Endoscopy, vol. 71, No. 7, pp. 1204-1210.
International Search Report for International Application No. PCT/US2010/059641, dated May 25, 2011, 5 pages.
International Search Report for International Application No. PCT/US2012/058679, dated Jan. 2, 2013, 3 pages.
International Search Report for International Application No. PCT/US2013/023401, dated May 7, 2013, 2 pages.
International Search Report for International Application No. PCT/US2014/016218, dated Apr. 4, 2014, 3 pages.
Marker Kit, "Gold fiducial markers—Accurate localization for soft tissue targets," Best Medical International, Inc. Springfield, VA, Jan. 2008, pp. 42-54.
PCT Notification of Transmittal of the International Search Report and Written Opinion of the International Search Authority, or the Declaration for PCT Application No. PCT/US2010/031842, dated May 6, 2010.
Specification of U.S. Appl. No. 62/009,587.
Specification of U.S. Appl. No. 62/012,789.
Office Action for U.S. Appl. No. 12/764,432, dated May 9, 2012.

\* cited by examiner

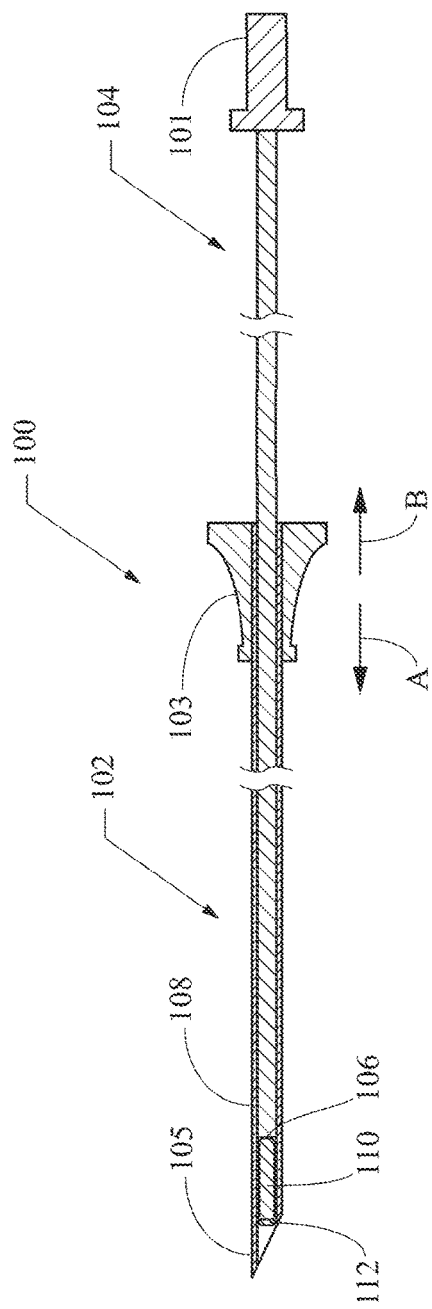
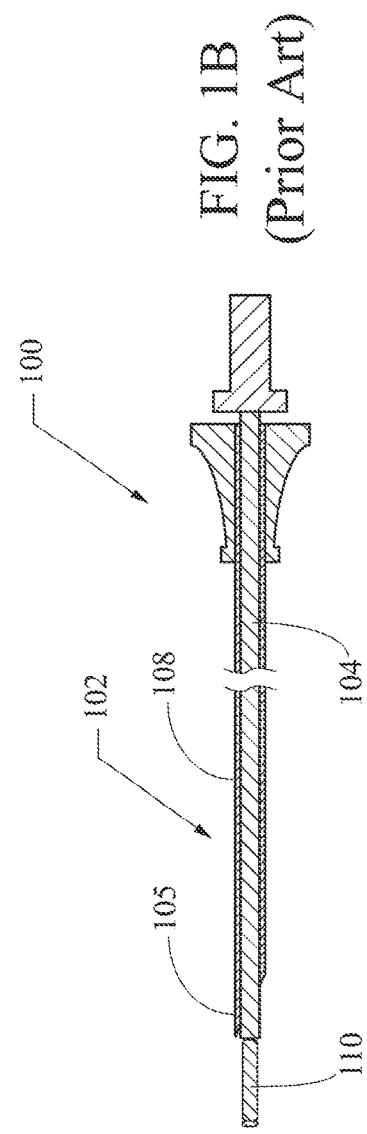
FIG. 1A (Prior Art)
FIG. 1B (Prior Art)

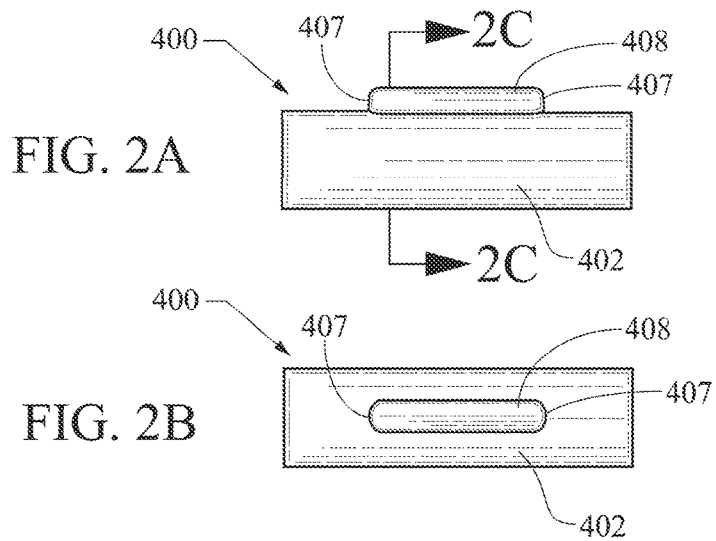
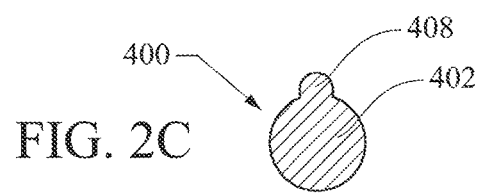
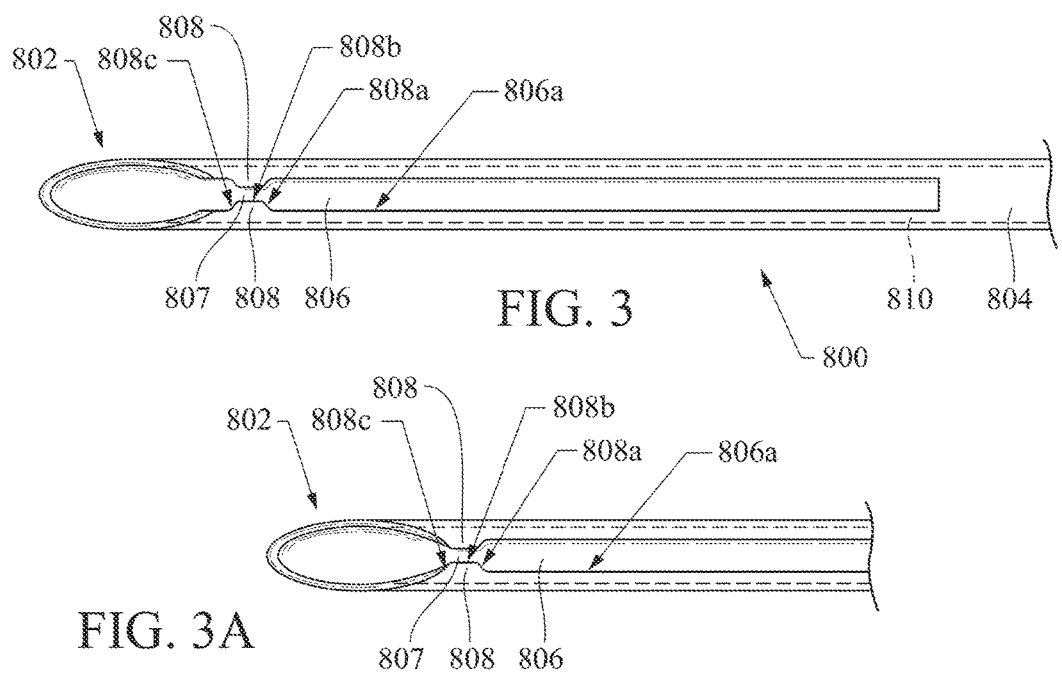

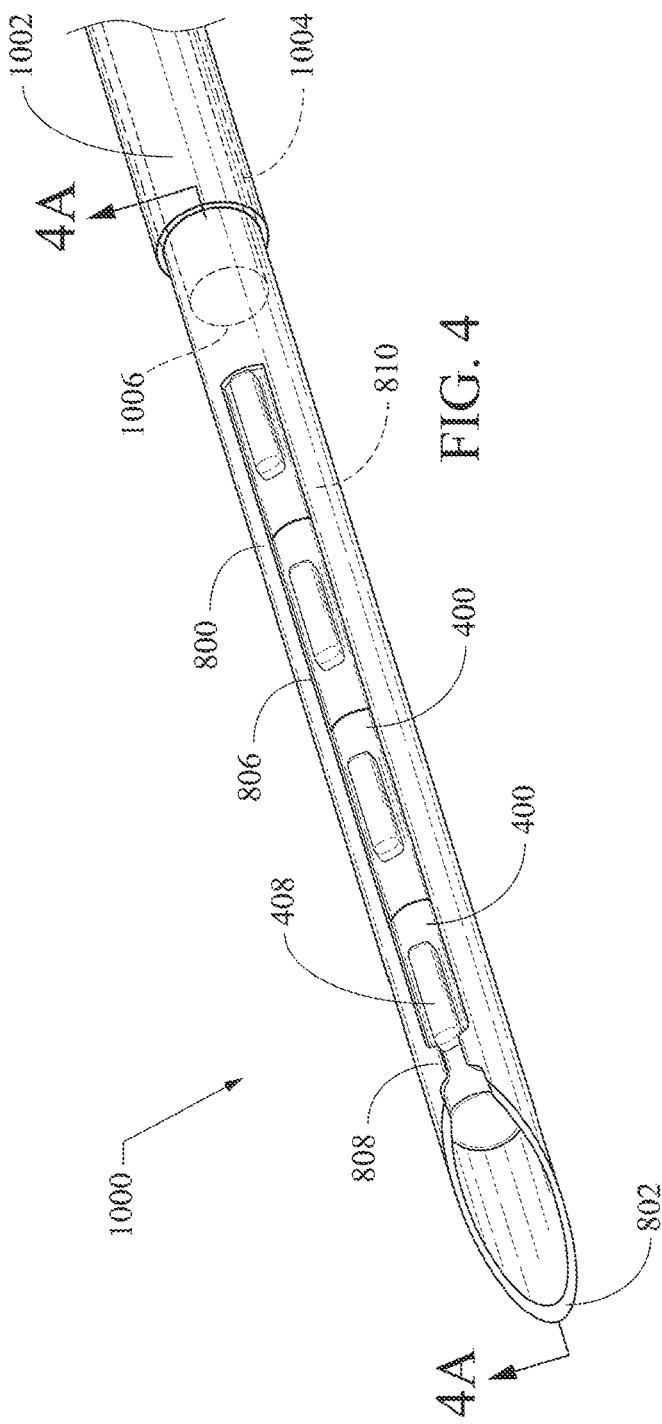
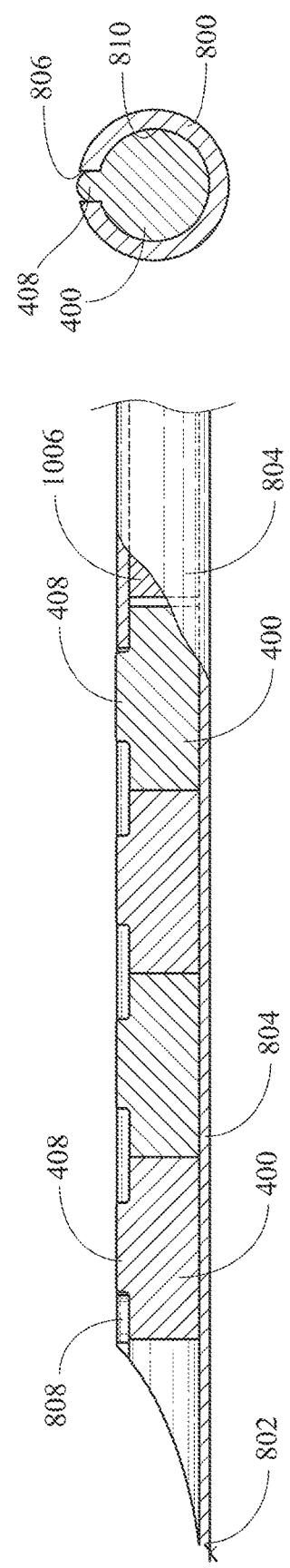

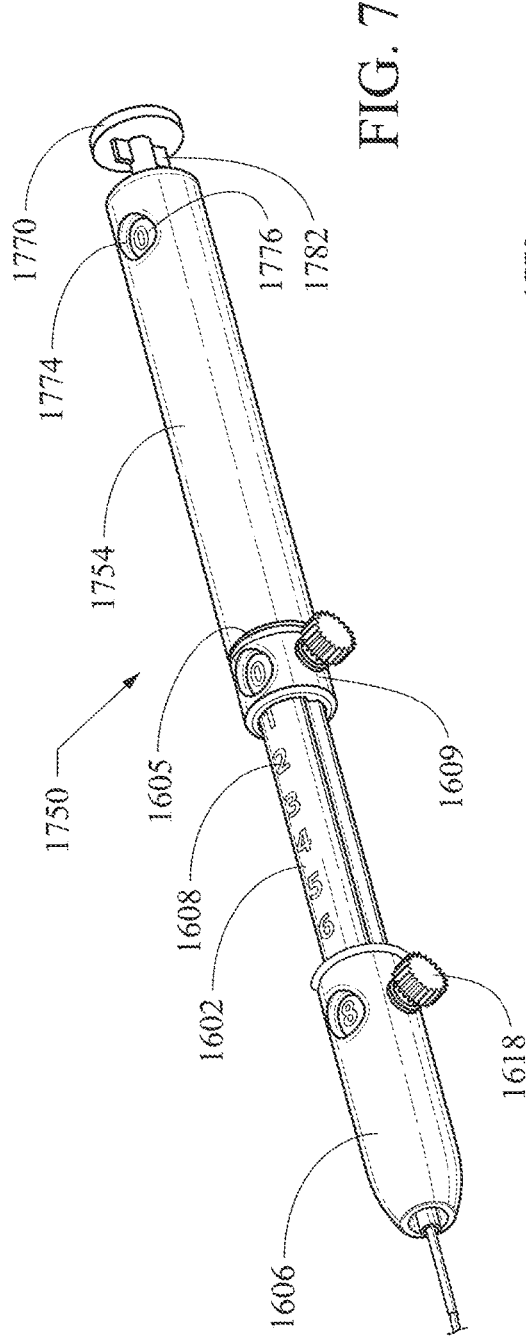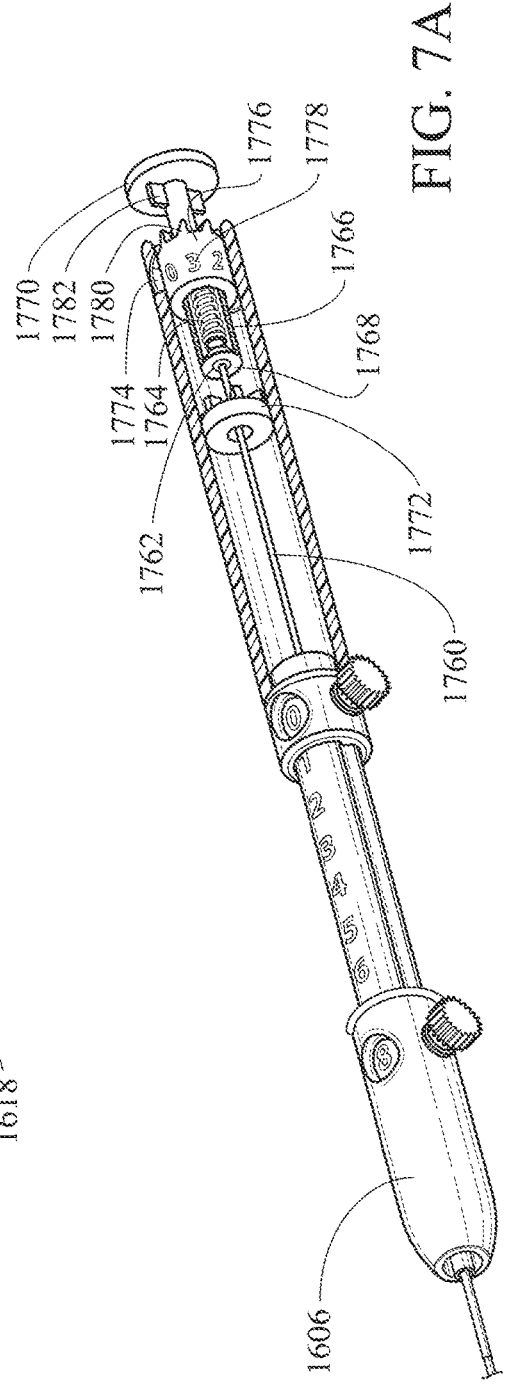

PLUNGER-DRIVEN COLLET HANDLE AND SYSTEM FOR FIDUCIAL DEPLOYMENT

CROSS-REFERENCE TO RELATED APPLICATIONS

This application is a U.S. non-provisional application which claims priority under 35 USC § 119 to U.S. provisional application Ser. No. 62/012,789, filed Jun. 16, 2014, which is incorporated by reference herein in its entirety.

TECHNICAL FIELD

Embodiments disclosed herein relate generally to a medical device system including one or more fiducials and methods of use for same. More particularly, the disclosed embodiments pertain to handle mechanisms and systems including same for endoscopically deploying fiducials, and methods of use for same.

BACKGROUND

Medical procedures often require locating and treating target areas within a patient. Focused, dose-delivery radiation therapy requires locating the target with a high degree of precision to limit damaging healthy tissue around the target. It is particularly important to know or estimate the precise location of the target in radiation oncology because it is desirable to limit the exposure of adjacent body parts to the radiation in a patient already suffering the depredations of cancer. However, in all treatment procedures, whether radiologic or otherwise, it is most desirable to be able to accurately target a region to be treated.

In many applications, it is not possible to directly view a treatment target or portion thereof (such as, for example, a cancerous tumor, cyst, pseudocyst, or other target) that needs to be acted on in some manner. As one example, when treating a lung or pancreatic tumor with radiation, it may not possible to view the actual tumor within the patient immediately before the radiation treatment. It is therefore highly advantageous to have some mechanism for permitting the tumor to be located accurately so that the radiation treatment can be targeted at the tumor while avoiding damage to healthy tissue.

Even for target regions that may be visualized using CAT (computer-assisted tomography) scans, MRI (magnetic resonance imaging), x-rays, ultrasound, or other techniques, difficulties often arise in targeting a treatment. This is particularly true for target regions within a torso of a patient and soft tissue regions. Due to the mobility of tissues in those regions (e.g., movement of internal organs during respiration and/or digestion, the movement of breast tissue with any change of body position, etc.), a target region may not remain fixed relative to anatomical landmarks and/or to marks that can be placed onto an external surface of a patient's body during one of those visualization procedures.

Several techniques have been developed to address this problem. One such technique is to place markers into the patient along the margins of the target region. The markers may be active (e.g., emitting some kind of signal useful in targeting a therapy) or passive (e.g., non-ferromagnetic metallic markers—called fiducials—that can be used for targeting under ultrasound, MRI, x-ray, or other targeting techniques, which may be included in a treatment device).

A fiducial is typically formed of a radio-opaque material that the target can be effectively located and treated with a device that targets a site using the fiducials as positional markers under radiographic detection. Typically, the fiducials may be inserted into the patient during a simple operation. Percutaneous placement is most commonly used. However, use of minimally-invasive placement via an endoscope has recently developed for fiducial placement into a patient's internal organs. For example, percutaneous placement of fiducials along the margins of a pancreatic tumor can be complex and painful (particularly for obese patients, where the needle size is necessarily larger). Another process using percutaneously implanted objects in a patient is brachytherapy. In brachytherapy, radioactive sources or "seeds" are implanted into and/or adjacent a tumor to provide a high dose of radiation to the tumor, but not the healthy tissue surrounding the tumor.

FIGS. 1A and 1B show longitudinal sectional views of a two-piece introducer 100 of the prior art useful for placement of brachytherapy seeds or fiducials. Referring first to FIG. 1A, the introducer 100 includes a needle 102 and a stylet 104 slidably disposed within the needle 102. The stylet 104 includes a first handle 101 and a blunt distal end 106. The needle 102 includes a second handle 103 and a bevel-tipped cannula 108 extending through the second handle 103. The cannula 108 is configured to hold a seed/fiducial 110. The cannula 108 has a distal tip 105 configured for percutaneous implantation of the seed/fiducial 110 into the patient.

In a "pre-loaded configuration," the seed/fiducial 110 is retained in the cannula 108 by a plug 112 made from bone wax or other suitable bio-compatible material(s). This is typically accomplished by a "muzzle-loading" technique where the fiducial is placed into the distal needle and then held in place by the bone wax plug. This can present some challenges, as the bone wax plug 112 can be visible as an artifact in the patient, potentially interfering with clear visualization of body structures or treatment devices. With this configuration, the cannula 108 must be withdrawn and reloaded after delivery of each seed/fiducial 110. If the target locations for the fiducials are very far apart, use of a single percutaneous introducer cannula/trocar for multiple introductions of the cannula 108 may not be possible. In such a circumstance, the patient must endure several percutaneous punctures (and the increased attendant risk of infection for each).

To implant the desired arrangement of seeds/fiducials 110 at a target location in a patient, an operator pushes the cannula 108 in a first direction (arrow A) to insert the tip 105 into the patient (typically under fluoroscopic visualization). The operator then pushes the second handle 103 further in the first direction to position the tip 105 at the desired depth within the patient where a seed/fiducial 110 is to be implanted. Throughout this motion, the operator moves the needle 102 and the stylet 104 together as a unit. At the desired depth/location, the operator grasps the first handle 101 with one hand and the second handle 103 with the other hand. Then, the operator holds the first handle 101 stationary while simultaneously sliding the second handle 103 back in a second direction (arrow B) toward the first handle 101. As shown in FIG. 1B, this movement causes the cannula 108 to retract over the seed/fiducial 110 to implant it in the patient. Alternatively, the operator may move the first handle 101 in the first direction (arrow A) while sliding the second handle 103 back in the second direction (arrow B). This causes the stylet 104 to push the seeds 110 out of the cannula 108. The procedure is then repeated to place other seeds/fiducials 110. When being used for targeting of radiation therapy, a minimum of three fiducials is typically required.

As will be appreciated from the disclosed structure, after deploying one fiducial, one may alternatively reload the introducer 100 from the proximal end by completely withdrawing the stylet 104, then placing another fiducial into the needle lumen and advancing it therethrough to a second location to which the distal needle tip 105 has been directed (a "breech-loading" technique). Provided that the fiducial target sites are sufficiently close together to allow this technique, it can reduce the number of percutaneous punctures or other access procedures needed to place more than one fiducial. However, it creates a problem for procedures where ultrasound is being used or is to be used in the near-future because it introduces air pockets into the tissue and related fluids. Those air pockets with tissue and/or fluid are echogenic in a manner that can interfere with ultrasound visualization of a target area and/or tools being used to diagnose or treat in/around the area. In some brachytherapy techniques, a series of fiducials may be preloaded into the needle—either separately or connected by a suture or similar device—then placed together in fairly close proximity; however, such a technique typically is not effective for placing three or more fiducials in sufficiently disparate locations to use for targeting a treatment relative to, for example, margins of a tumor. This may also be true for multifiducial systems that rely upon a distal plug to retain fiducials, which are thereafter released freely, in contrast with systems according to the present invention, which are configured for controlled serial release (e.g., one at a time, two at a time, or some other user-controlled retention and release of a pre-determined number of fiducials).

The process is similar when implemented endoscopically in the manner developed rather recently, except that the needle and stylet are of the type known in the art for use through the working channel of an endoscope. One limitation of current endoscopic techniques is the size of fiducial that can be introduced. With the size limitation of endoscope working channels, the largest needle that can typically be used without risking bending, crimping, curving or otherwise damaging a needle (that does not have an internal stylet or other support) during advancement out of the endoscope to an anatomical target is a 19-gauge needle. This limits the size of the fiducial that can be introduced through the needle lumen using current, cylindrical fiducials. The endoscopic technique generally suffers from the same reloading problems as described above. Even though the external percutaneous punctures are not an issue, having to withdraw and reload takes up valuable time and complicates the procedure, potentially requiring additional personnel, whether only the stylet is withdrawn for "breech-loading" or the entire device is withdrawn for "muzzle-loading."

It would be desirable to use ultrasound, and particularly endoscopic ultrasound (EUS) for navigation and placement of fiducials. As such it would be desirable to provide and use the largest possible fiducial that will provide improved echogenicity based on its size and echogenic profile. It would be desirable to provide multiple fiducials in a needle that can be introduced in a controlled serial manner (one, or some other pre-determined number, at a time) rather than requiring manual reloading after placement of each fiducial.

BRIEF SUMMARY

Embodiments of a fiducial deployment system described herein may include one or more of: one or a plurality of fiducials having one or more protuberances, a slotted needle configured for delivering a plurality of fiducials in serial fashion where the slot receives the fiducial protuberances without a detent that occupies any internal diameter needle lumen portion, a handle configured for controlling the serial delivery by user-operated deployment of a predetermined number of fiducials, and a method of delivering fiducials to a target region.

BRIEF DESCRIPTION OF THE DRAWINGS

FIGS. 1A-1B show a prior art fiducial introducer and method of use;

FIGS. 2A-2C show an embodiment of a fiducial from, respectively, top, side, and transverse section views;

FIG. 3 shows a top view of a slotted needle embodiment;

FIG. 3A shows a top view of another slotted needle embodiment;

FIGS. 4-4B show, respectively, a top perspective view, a longitudinal section view, and a transverse section view of a distal fiducial deployment system portion;

DETAILED DESCRIPTION

Figure 5A:
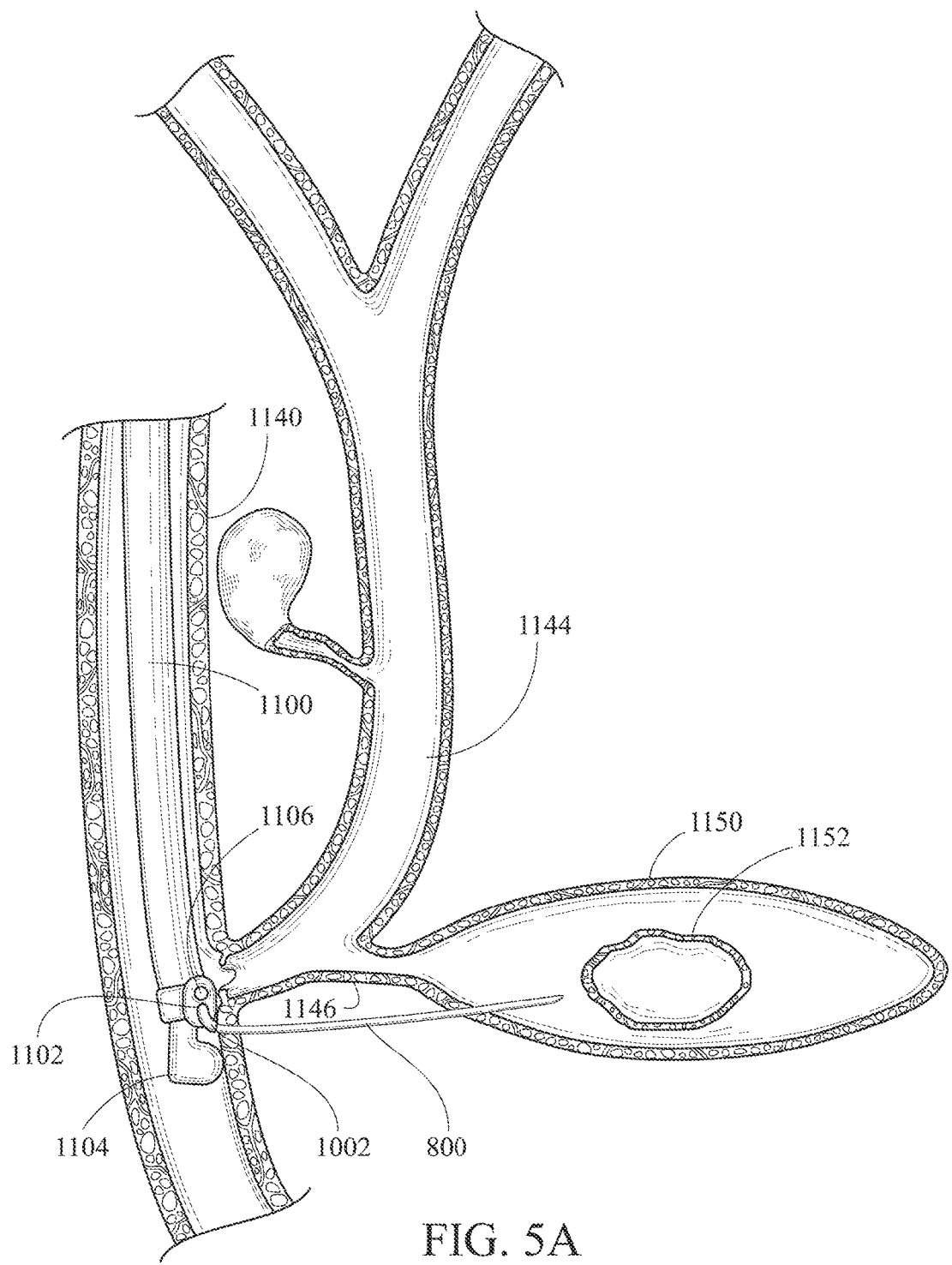
FIGS. 5A-5C show a method of placing fiducials.

The terms "proximal" and "distal" are used herein in the common usage sense where they refer respectively to a handle/doctor-end of a device or related object and a tool/patient-end of a device or related object.

A variety of fiducial and needle configurations may be used in keeping with the present embodiments including those described in U.S. Pat. App. Publ. Nos. 2010/0280367; 2011/0152611 to Ducharme et al.; 2013/0006101 to McHugo et al.; 2013/0006286 to Lavelle et al.; and 2013/0096427 to Murray et al., each of which is incorporated by reference herein in its entirety. One embodiment, illustrated with reference to FIGS. 2A-2C, of a fiducial 400 has a generally columnar body that is generally cylindrical with a generally circular transverse cross-section. A longitudinal surface face of the body may be dimpled to enhance its ability to reflect ultrasound waves and thereby provide a desirable echogenic profile. This dimpled characteristic may alternatively be embodied as a different irregular, patterned, or textured surface feature (e.g., knurled, ribbed) that may enhance the echogenicity of the fiducial 400, which will aid in visualizing it during EUS-guided placement, and allow it to be used in ultrasound visualization of a target site being marked by one or more fiducials 400 (e.g., a tumor).

Such a fiducial 400 preferably will be formed of a radio-opaque, non-ferromagnetic material such as, for example, gold, platinum, palladium, iridium, or alloys thereof, with one preferred embodiment including an alloy of palladium with rhenium (advantages of which may include desirable radio-opacity, market-price stability superior to gold, and ultrasound-reflectivity/echogenicity due to density). Being radio-opaque will allow the fiducial to be used in deployment techniques using fluoroscopy, as well as making it detectable/visualizable by radiographic means during a treatment or other procedure where it may be desirable to know the location(s) of one or more fiducials. Being non-ferromagnetic will lessen the likelihood that visualization techniques or other procedures employing magnetic fields such as, for example, MRI, will re-orient or otherwise dislodge a fiducial. Echogenic construction of a fiducial or needle may be enhanced by surface texture, but can also be provided by structural inclusions such as embedded bubbles or beads that provide for a different ultrasound reflectivity than material surrounding them. Fiducials may also be coated with a material (e.g., parylene) configured to reduce backscatter during radiography.

In a preferred embodiment, the fiducial 400 is configured and dimensioned for passage through and release from a needle lumen. For an endoscopic delivery system, the fiducial body 402 (exclusive of the protuberance) preferably will have an outer diameter (OD) of about the same or less than the inner diameter (ID) of a needle lumen, but the OD of the fiducial body preferably will be no greater than the needle ID. As used herein, the OD of the fiducial refers to an imaginary circle (or other geometric shape) whose outermost boundaries all fit within the ID of the needle lumen. In other words, it is preferable that the fiducial is dimensioned to fit slidably into the needle lumen, except the protuberance, which projects into the slot.

The longer body portion distal of the protuberance can help make certain that, during deployment through a needle, a first fiducial distal of this second fiducial will be fully advanced out of the needle before that second fiducial is positioned for deployment, as will be made clearer with reference to FIGS. 7-7G below. Accordingly, in many preferred embodiments, the fiducial protuberance (of the second and successive fiducials) will be nearer its proximal end than its distal end, so that the distal fiducial body portion projects sufficiently distally that it will advance the preceding first fiducial completely out of the needle lumen by the time that the second fiducial is in a position to be deployed (see FIGS. 4A-4C, 7D, 7E, and corresponding text). It should be appreciated that, even if all surfaces of the central fiducial portion 402 and protuberance 408 are generally smooth, the preferred materials forming the fiducial 400 and the presence of the protuberance 408 may provide a desirable echogenic profile that is readily visualizable under ultrasound at a resolution sufficient for locating and/or navigating it in a patient's body.

The fiducial 400 has a generally cylindrical body 402 formed as a mass with a generally circular transverse cross-section along its proximal and distal end sections. A protuberance 408 projects from the longitudinal circumferential face 406 of the fiducial body 402. As viewed from the top, the protuberance 408 is generally obround. The irregular shape and increased surface area (as compared to a typical cylindrical fiducial of the type used in plug-ended systems and/or systems with some type of lumen-occupying detent) preferably enhances the echogenicity of the fiducial, which preferably will already be desirably high due in part to its composition.

The protuberance 408 includes protuberance end faces 407 that may provide one or more of chamfered, filleted, and radiused transition to the outer face 406 of the body 402. The body 402 is generally a right cylinder, but for the protuberance 408. In this embodiment, the protuberance 408 is rounded and substantially parallel to the longitudinal central axis of the fiducial body, and it is about one half the length of the body 402, and it is centered along the body length. In a preferred embodiment, the fiducial 400 is configured and dimensioned for passage through and release from a needle lumen. For an endoscopic delivery system, the fiducial body (exclusive of the protuberance) will have an outer diameter (OD) of about the same or less than the inner diameter (ID) of a needle lumen, but the fiducial body OD preferably will be no greater than the needle ID. The protuberance 408 will engage and ride along through a needle slot.

Dimensions of one exemplary embodiment are also described with reference to FIGS. 2A-2C. In one exemplary embodiment the body 402 is about 0.12 inches (3.05 mm) long and has an OD of about 0.034 inches (0.86 mm). The protuberance 408 is about 0.06 inches (1.5 mm) long and is aligned along a midline of the body. The protuberance 408 projects about 0.008 inches (0.2 mm) above the OD of the body 402 and is about 0.011 inches (0.28 mm) wide. These measurements and proportions may be varied in other embodiments while remaining within the scope of the presently-claimed material. For example, the protuberance may be more distally or proximally located, and may be at an angle relative to the midline such that it partially spirals around the outer surface of the body.

FIG. 2C shows an end view of a transverse section taken along line 2C-2C of FIG. 2A. It shows one embodiment of general proportions of a fiducial body and protuberance of the present system.

FIG. 3 shows an embodiment of a fiducial introduction needle 800. The needle 800 is illustrated with a beveled distal tip 802. Its tubular cannula body 804 includes a longitudinal needle slot 806 along a distal end region of the cannula 804. The slot 806 preferably includes at least one detent including at least one detent surface, and more preferably two detents. The slot 806 is shown as being open through the entire wall of the cannula 804, but it should be appreciated that the slot may extend less than the thickness of the needle wall, such that it is embodied as a groove.

In the embodiment of FIG. 3, the detent is formed as a narrowed portion 807 of the slot 806 between two tabs 808. The tabs 808 are generally trapezoidal, but may have a different geometry in other embodiments. As shown in FIG. 3A, in certain preferred embodiments, the tabs 808 may be located immediately adjacent the distal bevel (e.g., to maximize efficiency of advancing a fiducial past them and out of the needle while minimizing residual overlap of a deployed fiducial with the beveled portion of the distal needle tip). Each of the transitions between the edge 806a of the needle slot 806, the proximal tab edge 808a, central tab edge 808b, and distal tab edge 808c may be cornered (e.g., chamfered or filleted) or rounded (e.g., radiused). The tabs 808 preferably are near the distal end of the slot 806.

The body wall cannula 804 generally circumferentially defines a needle lumen 810 configured to allow sliding passage therethrough of a fiducial such as, for example, a fiducial (e.g., as shown in FIGS. 2A-2C or others that would readily pass through the needle lumen 810, preferably with controllable retention of the fiducial(s) by the tabs 808). The needle may be constructed from a nickel-titanium alloy, cobalt-chromium (CoCr) alloy, stainless steel or any other suitable material. Its tip may have a different geometry than the beveled configuration shown. In an alternative embodiment, the tabs 808 may meet such that they will be forced to flex upward and/or outward to a greater degree to allow passage of a protuberance on a fiducial. And, the outer surface of the needle may be dimpled or otherwise textured to provide enhanced echogenicity.

An exemplary needle embodiment is also described with reference to FIG. 3, which exemplary needle embodiment may be configured and dimensioned for use with the exemplary fiducial embodiment described above with reference to FIGS. 2A-2C. In one such exemplary needle embodiment, the ID of the needle lumen is at least about 0.034 inches (0.86 mm). The OD of the needle is about 0.042 inches (1.07 mm; about 19-gauge), with a wall-thickness of about 0.008 inches (0.2 mm). The slot portion proximal of the tabs is about 0.02 inches (0.5 mm) wide and about 0.42 inches (about 10.7 mm) long. Each of the tabs extends about 0.06 inches (0.15 mm) out of the slot edge and has a slot-facing edge that is about 0.02 inches (0.5 mm) long (not including the proximal and distal angled transitions from the slot edge, which are radiused at about 0.005 inches (0.13 mm)). These measurements and proportions may be varied in other embodiments, including those illustrated herein, while remaining within the scope of the presently-claimed material. For example, the particular dimensions of a slot, tabs, and fiducial may be configured for use with a 22-gauge needle having a desirable balance of flexibility and stiffness, as well as including a distal needle tip bevel of about 30°, a slot width of about 0.014 inches (about 0.36 mm) with slot tabs separated only by about 0.006 inches (about 0.15 mm) across the slot, and echogenicity-enhancing surface dimpling disposed along the needle exterior adjacent and generally parallel with at least a distal length of the slot.

The distal end portion of a fiducial deployment system 1000 is described with reference to FIG. 4, which is an external view, FIG. 4A which is a longitudinal section view taken along line 4A-4A of FIG. 4, using the needle 800 and fiducial 400 described above, and FIG. 4B, which shows a transverse section view along line 4B-4B of FIG. 4A. The system 1000 includes a flexible elongate needle sheath 1002. The needle 800, including a more flexible proximal body portion 820 extends through a sheath lumen 1004. At least one fiducial 400, illustrated here as a plurality of fiducials 400, is disposed slidably removably in a distal region of the needle lumen 810 of the needle's cannular body. The central longitudinal body portion 402 substantially occupies the inner diameter of the needle lumen 810. The protuberance 408 of each fiducial 400 has a height that may be about the same as the thickness of the needle wall, including the slot 806 into which the protuberances 408 project.

The protuberance 408 of the distal-most fiducial 400 is captured against the tabs 808 of the needle 800. A stylet 1006 configured for use as a pusher is disposed through a portion of the needle lumen 810 and preferably is configured for actuation from the proximal end, whereby it can be used to distally advance/push out the fiducials and/or hold them in place as the needle is withdrawn from around them. The presence of the fiducials and stylet in the needle 800 preferably improve its columnar strength reduce the likelihood that it will get bent, crimped, or otherwise damaged as it is navigated through and out of the distal end of an endoscope working channel (not shown).

FIG. 4B shows a transverse section end view of a section of a needle 800 (as in FIG. 3) and a fiducial 400 (as in FIGS. 2A-2C). This view shows the preferred close tolerances and a preferred orientation of the fiducial body relative to the needle lumen 810 and the protuberance 408 relative to the needle slot 806.

Several different handle embodiments may be used to effect advancement and release of one or more fiducials. Certain handle embodiments are described with reference to FIGS. 7-7G below, including with reference to the structure and method described below with reference to FIGS. 4-4B and 5A-5C.

A method of using the fiducial deployment needle of FIGS. 4-4B is described with reference to FIGS. 5A-5C, with reference to the structures shown in greater detail in FIGS. 4-4B. In a preferred method of use, an endoscope 1100 is provided, including a working channel 1102. In one preferred method, the endoscope is an EUS endoscope including a distal ultrasound array 1104 configured for ultrasound imaging. The endoscope 1100 preferably also includes a video element 1106 (e.g., CCD, optical camera, or other means for optical visualization). The methods below are described with reference to placing fiducials 400 at the margins of a tumor 1152 of a patient's pancreas 1150, such that the needle body will be of sufficient length and navigability (e.g., pushability and flexibility) to perorally directed through a patient's gastrointestinal tract to a target site, including doing so via a working channel of an endoscope such as a gastric endoscope, colonoscope, anuscope, or other visualization/procedure-assisting device.

Figure 5B:
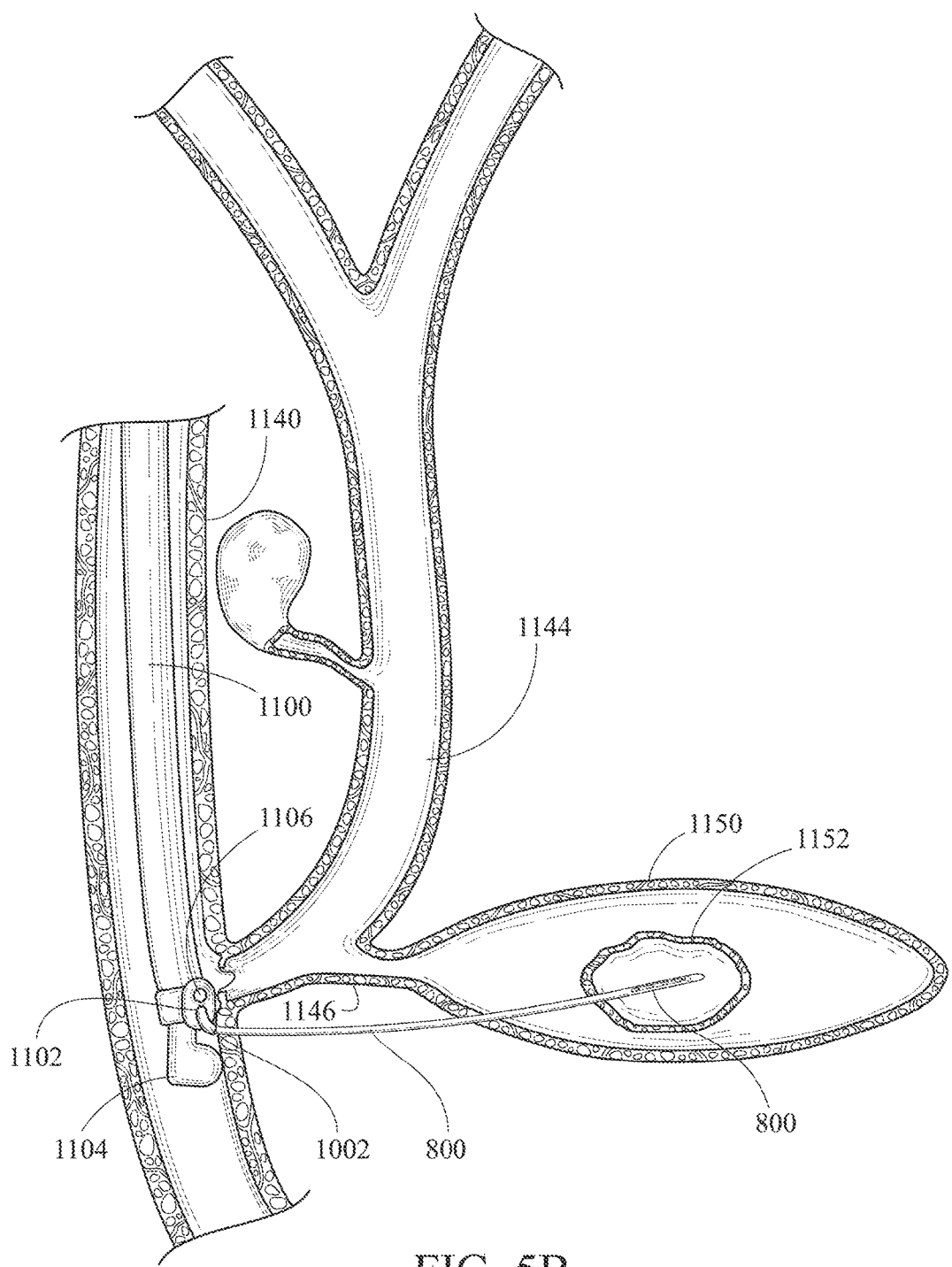
Figure 5C:
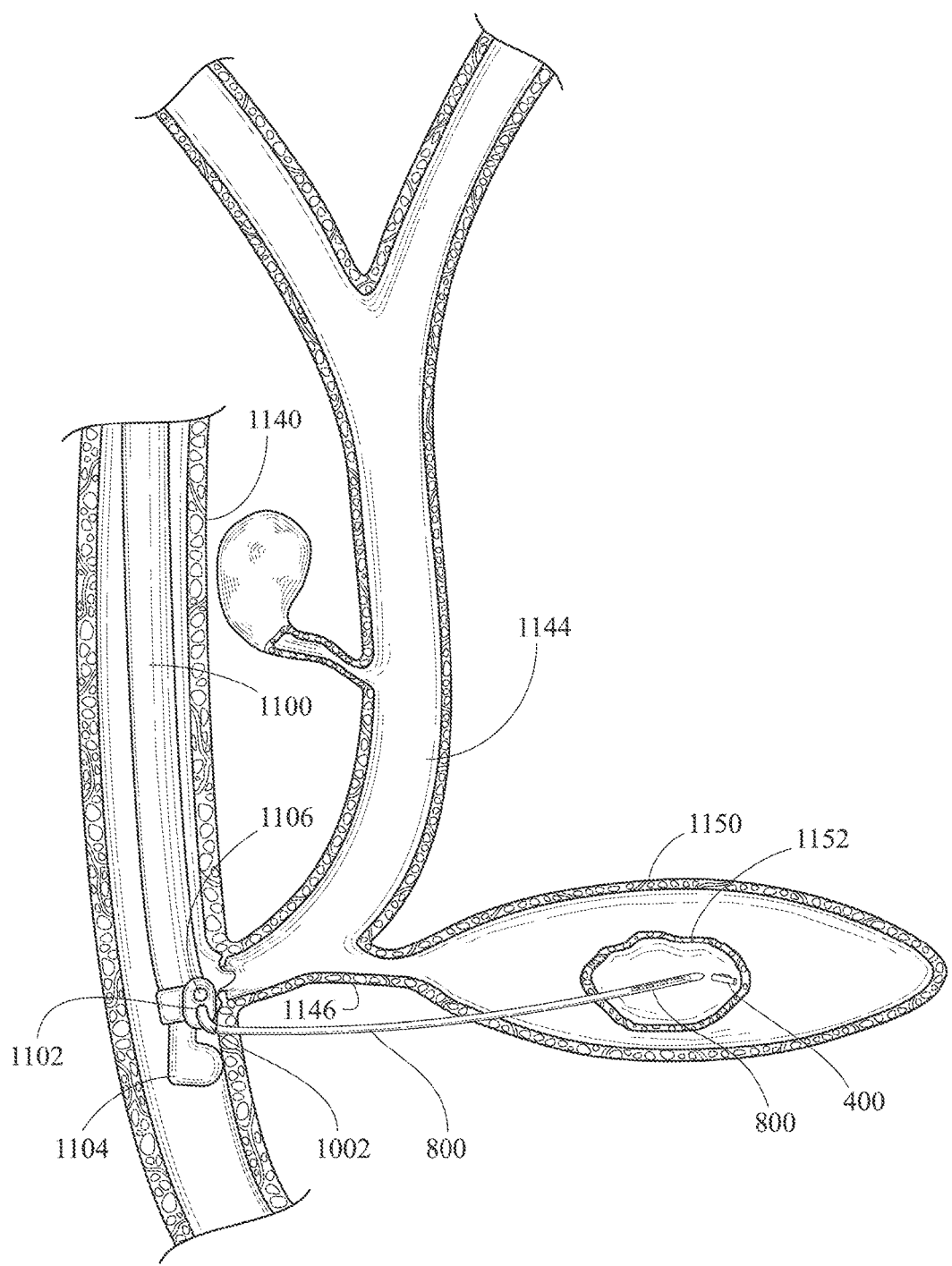

The endoscope 1100 is shown in FIG. 5A as having been directed through a patient's duodenum 1140 until its distal end portion is adjacent the Sphincter of Oddi 1142, which provides access to the common bile duct 1144 from which the pancreatic duct 1146 branches and leads to the pancreas 1150.

As shown in FIG. 5A, the sheath 1002 has been advanced to the duodenal wall and the needle 800 has been pierced therethrough, extending near the pancreatic duct 1146 to a location adjacent the tumor 1152 in the pancreas 1150. As shown in FIG. 5B, the needle 800 is directed to a first target site at a margin of the tumor 1152 (preferably under ultrasound guidance, which can be replaced, complemented, and/or verified by fluoroscopy or another visualization technique). Once the distal end 802 of the needle 800 is positioned at the first target, the distal-most fiducial 400 therein is deployed. In one aspect, the deployment may be accomplished by positioning the distal needle end 802 and the fiducial 400 therein at the first target, then retracting the needle 800 while retaining the position of the stylet 1006 such that the fiducial 400 remains in the desired first target position. In another aspect, the deployment may be accomplished by positioning the distal needle end 802 and the fiducial 400 therein adjacent the first target, then holding the needle 800 in position while advancing the stylet 1006 such that the fiducial 400 is advanced into the desired first target position.

As will be appreciated from the structure of the needle 800 and fiducials 400 as shown in FIGS. 4-4B, a user preferably will be able to control advancement/deployment of the fiducials to one at a time, such that a plurality of fiducials (without any spacers) may serially—but separately and independently—directed into different locations. Then the fiducial 400 is in a "ready to deploy" position, its distal protuberance face 408a is engaged against the proximal tab edges 808a. To deploy the fiducial 400, the user must move one of the stylet 1006 or needle 800 relative to the other with sufficient force to advance the protuberance 408 through the tabs 808.

The user preferably will have a tactile sense of resistance as the protuberance 408 passes through the tabs 808, which resistance will decrease immediately as soon as the protuberance clears the tabs. Then the user preferably continues the relative motion of stylet and needle until resistance is again encountered, indicating that the next fiducial behind the distal-most one has met the proximal tab edges 808a.

It will often be preferred that the fiducials (and the protuberances thereon) be proportioned such that complete deployment of a distal-most fiducial includes it substantially clearing the distal needle tip 802 and coincides with the protuberance of the next distal-most fiducial meeting the proximal tab edges 808a. As such, it may be advantageous in some fiducial embodiments to position the protuberance more proximally on the fiducial body such that a fiducial body portion distal of the protuberance is longer than a body portion proximal of the protuberance. It should be appreciated that the protuberance of almost any fiducial embodiment in keeping with principles of the present invention may be disposed near the proximal end up to and including flush with the proximal end of the fiducial body). FIG. 5C shows the fiducial in place, with the needle withdrawn away from it.

Next, the user may retract the needle 800 into the sheath 1002 to a sufficient distance allowing it to be re-extended to a second target site, where the procedure described above may be repeated. These steps may be repeated for placement of third, fourth, and further fiducials. As is known in the art, these fiducials may be used for "positive targeting" and/or "negative targeting" of a therapy such as radiation therapy ("positive targeting" indicating "treat here", and "negative targeting" indicating "do not treat here"). The present system presents numerous advantages. For example, consider a patient already undergoing an endoscopy procedure to biopsy a located but undiagnosed tissue mass. The endoscopic biopsy can be taken and a tissue slide prepared immediately. If a diagnosis is made (in conjunction with whatever other data are available and pertinent) that the tissue mass will benefit from a treatment where placement of fiducials is indicated, the physician can immediately deploy fiducials in the manner described above.

The ability to complete the method using direct/video and ultrasound imaging with little or no use of fluoroscopy presents an advantage of minimizing the radiation exposure of the patient (who may, for example, have to undergo radiation therapies where the total amount of exposure to radiation is desired to be minimized to that which is therapeutically and diagnostically necessary). Advantages of time and expense for the patient, physician and other treating/diagnostic personnel, and the treatment facility are likely as implementation of the present method may prevent all of those entities from having to schedule and conduct a second endoscopic procedure, and/or to extend the initial diagnostic procedure with the time-consuming methods and materials currently available in the prior art as described. It should also be appreciated that, when informed by the present disclosure, those of skill in the art may utilize and/or adapt the presently-disclosed embodiments for percutaneous use while remaining within the scope of one or more claims.

Fiducials with generally cylindrical or otherwise generally regular geometry may migrate after having been placed in a desired location, including that—over the course of multiple treatments of a target area delineated by fiducials—they may migrate with changes in the condition of surrounding tissues. For circumstances where it may be advantageous to minimize migration, a fiducial may be used that includes one or more anchoring projections.

Figure 6A:
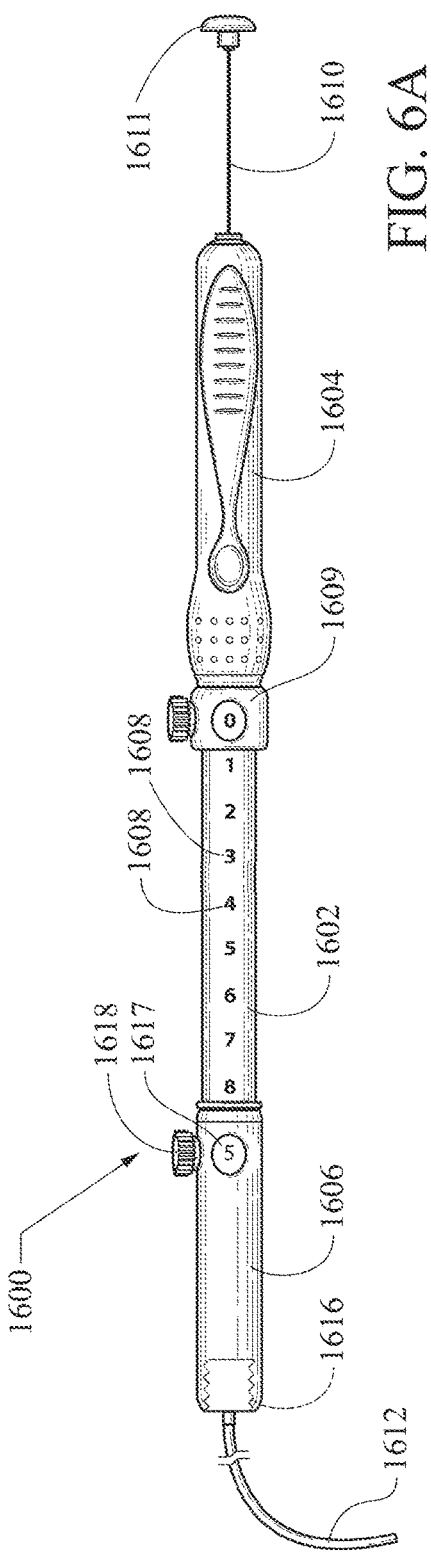
FIGS. 6A-6B show a handle embodiment for a fiducial deployment system.
Figure 6B:
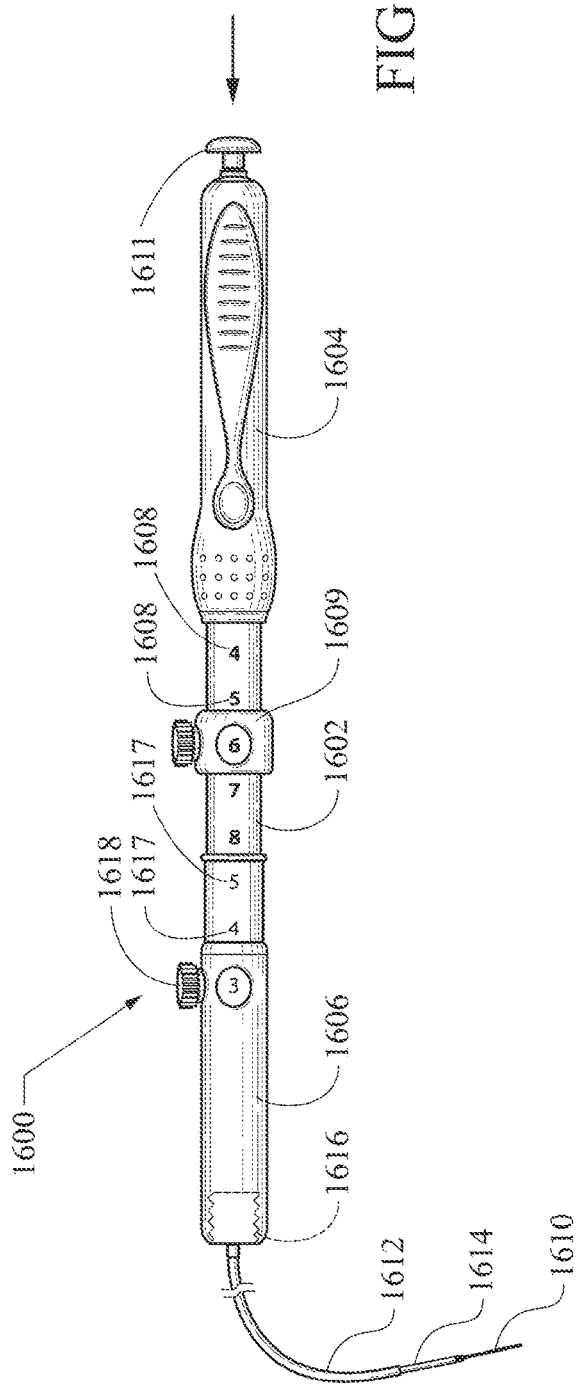

FIGS. 6A-6B show a handle embodiment 1600 that may be used with a fiducial deployment system. The handle 1600 includes a sheath-attached handle member 1602 with a needle-attached handle member 1604 longitudinally slidably disposed on its proximal end. A handle member 1606 (which may be configured for scope-attachment) is slidably attached to the distal end of the sheath-attached handle member 1602. The sheath-attached handle member 1602 is attached to the needle sheath 1612 and the needle-attached handle member 1604 is attached to the needle 1614 (which may be configured in the manner of any of the needles disclosed herein or later developed in accordance with principles of the present disclosure). The scope-attachment handle member 1606 is configured for incrementally-fixable, longitudinally-adjustable (relative to the other handle components) attachment to the exterior of an endoscope working channel (not shown) using, for example, a threaded cavity 1616. The scope-attachment handle member 1606 allows a user to determine the distance by which the sheath 1612 will extend from a standard-length endoscope, and it may include numerical or other indicia 1617 corresponding to that relative length and an adjustable engagement structure 1618 allowing a user to select a length and engage the scope-attachment handle member 1606 accordingly. It should be appreciated that embodiments of the handle described and claimed herein may be practiced within the scope of the present invention without including a scope-attachment member.

The sheath-attached handle member 1602 includes numerical indicia 1608 and an adjustable ring 1609 that limits the movement of the needle-attached handle member 1604 and provides a way to select the distance to which the needle 1614 may be extended beyond the sheath 1612. By way of illustration, the configuration shown in FIG. 6A would allow the sheath to extend 5 units (e.g., inches, cm) beyond the distal end opening of an endoscope working channel, and the needle 1614 would not extend at all beyond the distal end of the sheath 1612. The configuration shown in FIG. 6B would allow the sheath to extend 3 units (e.g., inches, cm) beyond the distal end opening of an endoscope working channel, and the needle 1614 would be allowed to extend up to 6 units beyond the distal end of the sheath 1612, although its current position would be only about 4 units beyond the distal end of the sheath 1612.

A stylet 1610 extends through a lumen of the needle 1614 and has a stylet cap 1611 fixed on its proximal end. The stylet 1610 is shown as being retracted proximally in FIG. 6A, and extended beyond the distal end of the needle 1614 in FIG. 6B. The stylet 1610 may be manually advanced distally through the needle lumen in the same manner as described above (with reference to FIGS. 4-4B) for a stylet 1006. As such, a user may use the stylet to manually push fiducials out of a distal end of the needle 1614. If this method is used (e.g., in the manner described above for deployment of fiducials with reference to FIGS. 4-5C), a user may rely upon tactile feedback to determine when a fiducial has been advanced beyond any detents, which may be difficult through a long stylet—particularly if the detents are rounded such that the advancing motion is relatively smooth. Accordingly, it may be advantageous to provide an advancement mechanism configured to attach to (including being integrated with) the handle 1600 that provides improved control of stylet advancement.

Figure 7B:
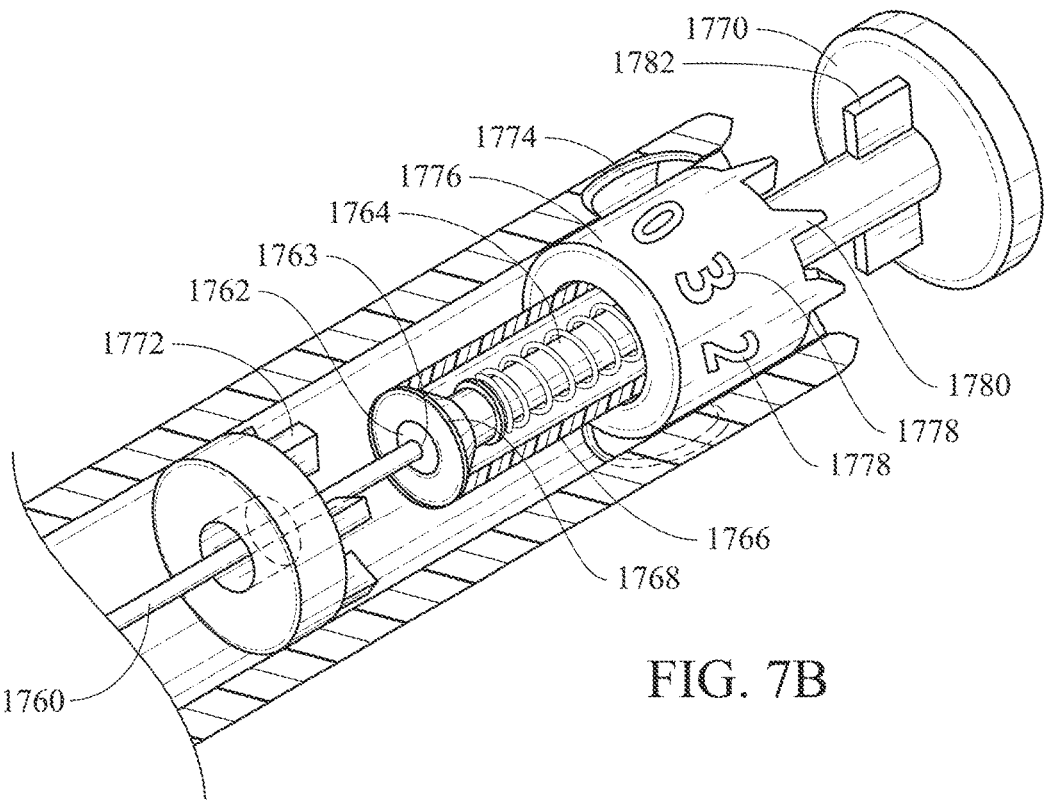
FIGS. 7-7G show, respectively, an external view, an internal-component view, and method-of-use/function views of an advancement mechanism embodiment for a fiducial deployment system.
Figure 7C:
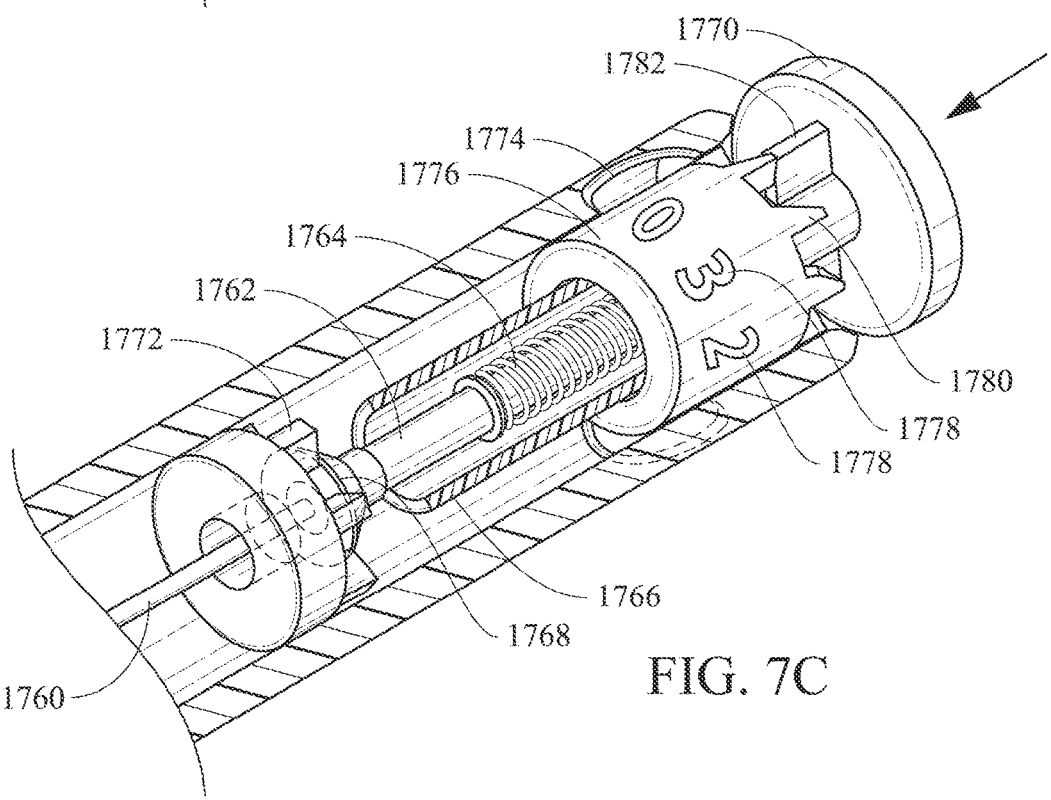
Figure 7D:
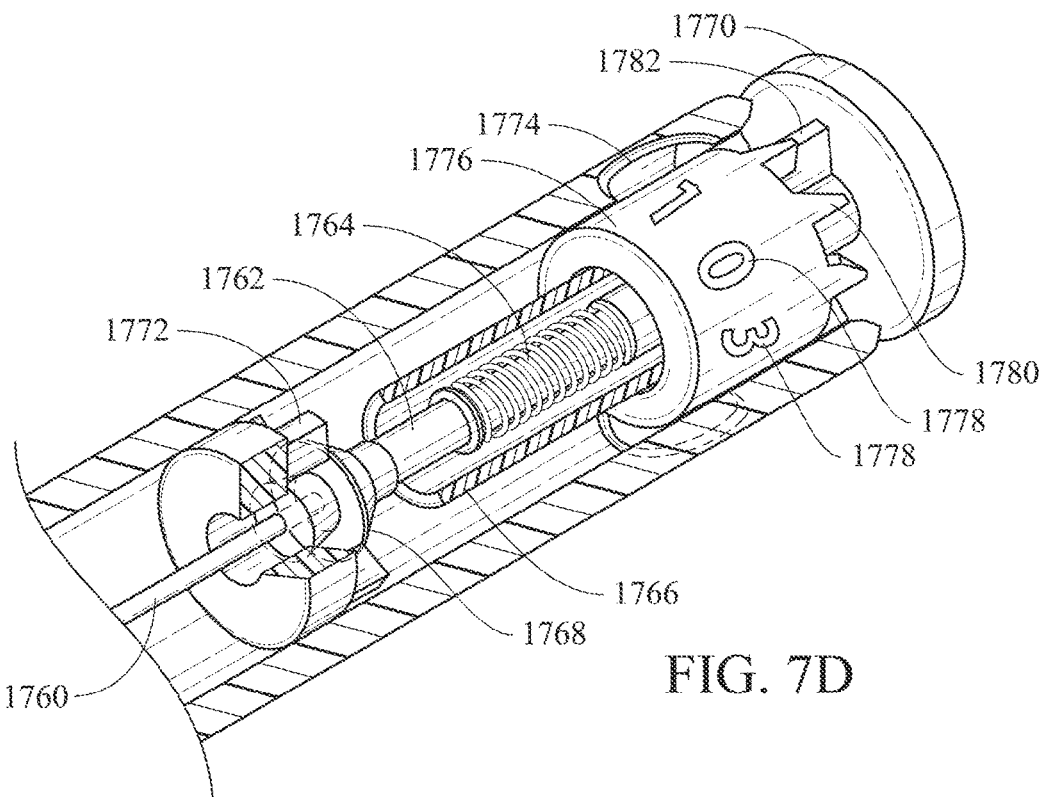
Figure 7E:
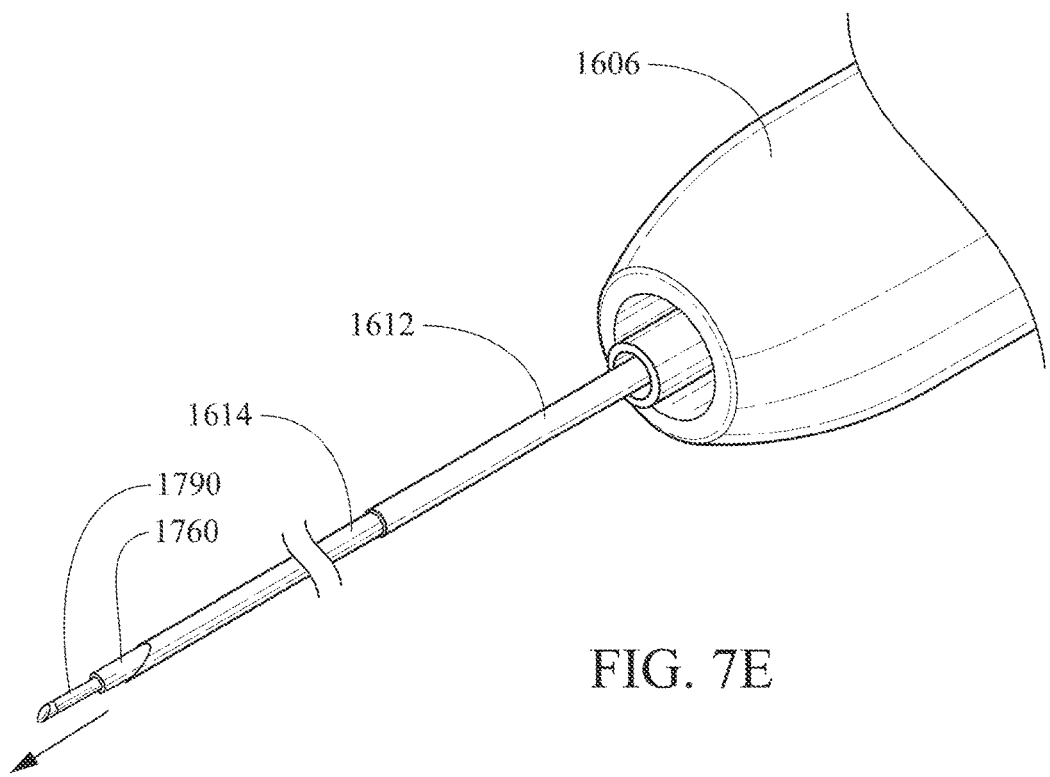
Figure 7F:
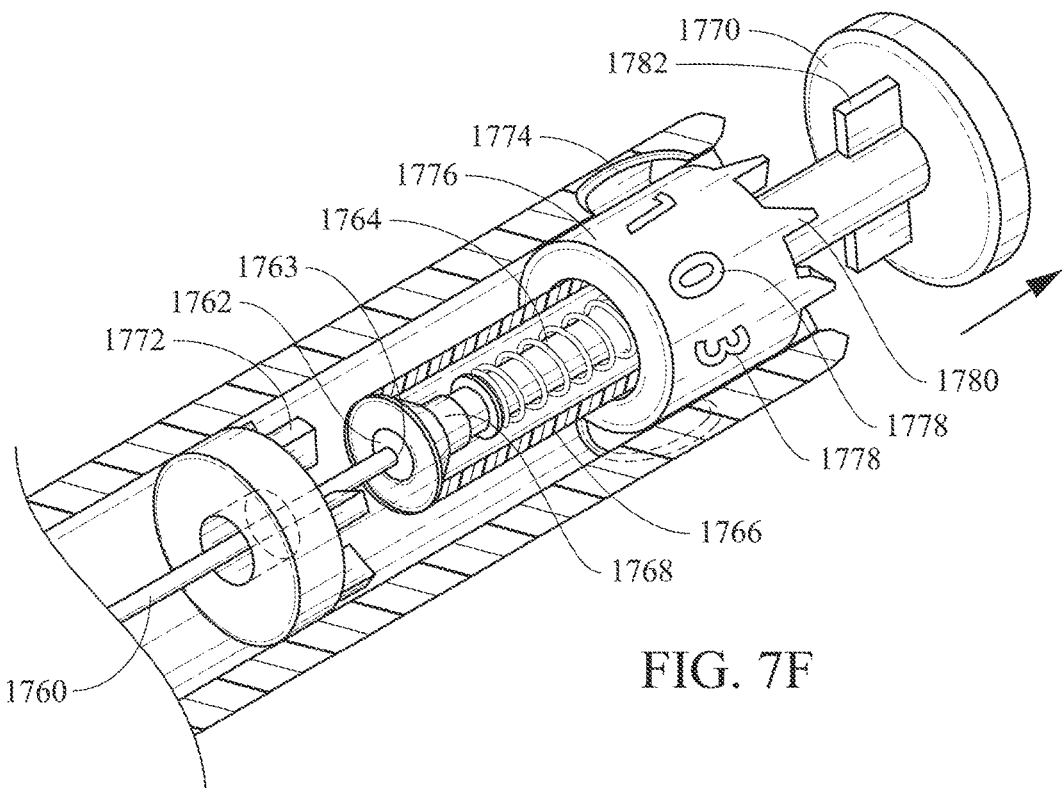
Figure 7G:
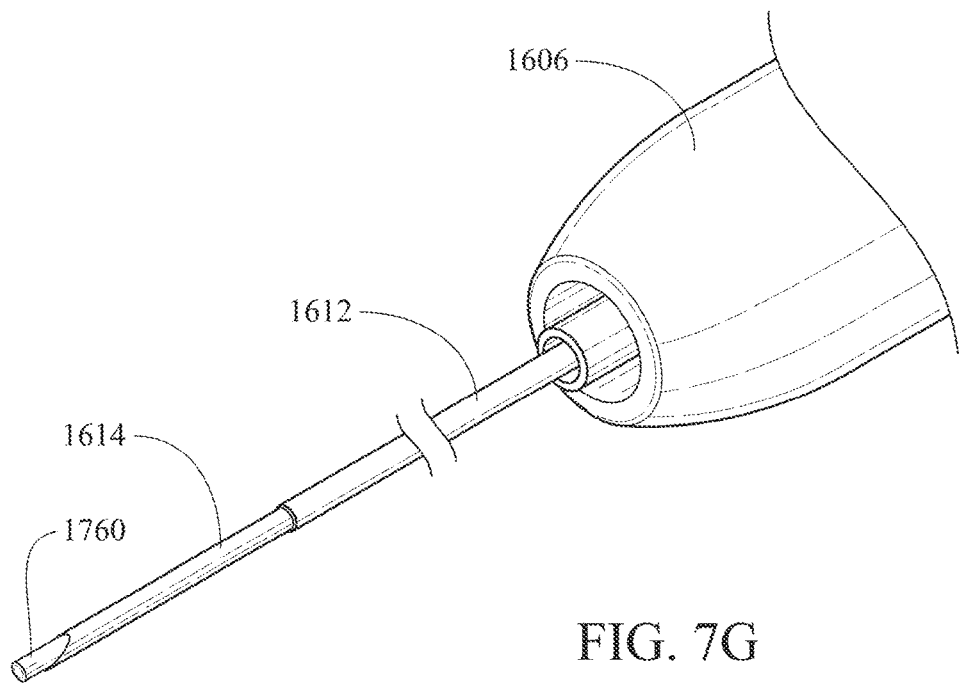

FIGS. 7-7G show embodiments of advancement mechanisms that may be used with handle assembly configurations similar to those of FIGS. 6A-6B, or other handle configurations (including, for example, those disclosed in U.S. Pat. App. Publ. Nos.: 2010/0280367 and 2011/0152611 to Ducharme et al.; 2013/0006101 to McHugo et al.; 2013/0006286 to Lavelle et al.; and 2013/0096427 to Murray et al). FIGS. 7-7G show a plunger-driven handle component 1750 for a fiducial deployment system. In this and other embodiments, the handle component 1750 may be removably or permanently attached to, or otherwise integrated with, a proximal end of a handle, such as proximal end 1605 of needle-attached handle member 1604 shown in FIGS. 6A-6B, where it will provide means for controlled advancement of a stylet (e.g., stylet 1610) in lieu of direct and/or manual manipulation of the stylet cap 1611. In some embodiments, the handle component 1750 may be removably or slidably attached to a proximal end of sheath-attached handle member 1602 and may be used in lieu of, or integrated with, needle-attached handle member 1604 (internal needle elements of which are not shown in FIGS. 7-7G for the sake of clarity in illustrating the present embodiments), such that the slidable distance of sheath-attached handle member 1602 may be controlled by adjustable ring 1609.

The plunger handle component 1750 may include at least one actuating plunger member 1770 embodied as a longitudinally slidable plunger and an elongate first handle member body 1754 that includes and defines a central longitudinal axis and a handle lumen. Plunger handle component 1750 may be attached directly or indirectly to a cannula (e.g., needle and/or sheath), such as via an elongate distal outer body having a longitudinal body lumen (e.g., in some embodiments, sheath-attached handle member 1602, or, in other embodiments, a fiducial needle and/or sheath). A stylet 1760 (which may correspond to the stylet 1610) extends through at least a portion of the first handle member body 1754 along or generally aligned with its central longitudinal axis.

A user-operable portion of the actuating plunger member 1770 is movably disposed on the proximal end of the first handle member body 1754 and extends longitudinally through at least a portion of the handle's central longitudinal axis and the handle lumen. The actuating plunger member 1770 is attached to or otherwise engaged with an elongate collet 1762 that likewise includes and defines a central longitudinal axis and a collet lumen 1763. In some embodiments, the collet 1762 may be formed having a cylindrical inner surface defining the collet lumen and conical outer surface. A collar 1768 includes and defines a central longitudinal axis and a collar lumen and is removably or slidably engaged surrounding the distal end of the collet 1762. The stylet 1760 extends through at least a portion of the collet 1762 and the collet lumen 1763 along or generally aligned with its central longitudinal axis. The distal end of the actuating plunger member 1770 is engaged by and biased or urged toward the proximal end of first handle member body 1754 by a compression spring 1764, although those of skill in the art will appreciate that this proximal-directed tendency may be accomplished by a variety of means without exceeding the scope of the present disclosure.

While at rest, the actuating plunger member 1770 is held in a fully pulled back position, as depicted in FIGS. 7A and 7B, by the proximal-directed tendency of compression spring 1764. In this position, at least a portion of collet 1762 is contained within elongate stopper housing 1766, which includes and defines a central longitudinal axis and a housing lumen. The stopper housing 1766 further defines a first laterally protruding upper stopping lip and a second laterally protruding lower stopping lip at the distal end of the housing lumen along or generally aligned with its central longitudinal axis. The upper stopping lip of stopper housing 1766 is engaged by the distal end of the compression spring 1764. The proximal end of compression spring 1764 engages the distal end of the actuating plunger member 1770. While at rest, the compression spring 1764 exerts force sufficient to hold the actuating plunger member 1770 in a fully pulled back position within handle member 1754.

When the actuating plunger member 1770 is in fully pulled back position, the collar 1768 is at least partially contained within the distal end of the stopper housing 1766 and is engaged by the lower/distal end terminal surface defining a stopping lip of the stopper housing 1766. A laterally protruding buffer plate 1772 is also formed on an inner wall of the handle lumen of the first handle member body 1754. Buffer plate 1772 defines at least one or more laterally protruding stopping lips disposed within the handle lumen and having a hollowed out center or buffer lumen generally aligned with the longitudinal axis of the first handle member body 1754. In one embodiment, as shown in FIGS. 7A-7D and 7F, the laterally protruding stopping lip(s) of the buffer plate 1772 may be formed as a series of box-like pegs laterally protruding from the interior wall of the handle lumen, but those of skill in the art will appreciate that this laterally protruding stopping lip may be accomplished by a variety of means without exceeding the scope of the present disclosure.

The plunger member 1770 also defines vertically protruding actuating members—embodied here as pegs 1782—on the distal edge of the plunger member 1770, which, during user operation, may engage one or more vertically protruding actuating members formed on the proximal end of the rotationally driven indicator dial 1776. In one embodiment, as depicted in FIGS. 7-D and F, the vertically protruding actuating members formed on the proximal end of the rotationally driven indicator dial 1776 are embodied as biased or tapered teeth 1780 that are angled by a predetermined degree and length, although those of skill in the art will appreciate that actuation of the rotationally driven indicator dial 1776 may be accomplished by a variety of means without exceeding the scope of the present disclosure. The outer surface of the indicator dial 1776 is shown in the figures as having numerical indicia 1778 that can be seen through a window 1774 formed in the body of the handle member body 1754. Numerical indicia 1778 (which in other embodiments may be colored bands or other similar visual indicia) may be used to provide a visual cue to the user allowing the user to identify information about the distance advanced by the stylet's distal end from actuation of the plunger member 1770.

With this structure disclosed, those of skill in the art will appreciate a method of use. FIGS. 7B-7G show perspective, generally longitudinal views of internal components, including a method of operation for this embodiment. Distal advancement of plunger member 1770 and stylet 1760, corresponding to a fiducial-deployment or other stepwise/incremental distal stylet movement action is shown in an exemplary partial distal needle view of FIGS. 7D and 7E (see also, e.g., FIGS. 5B and 5C). As shown in FIG. 7B, the plunger member 1770 may be actuated and depressed causing the vertical actuating pegs 1782 protruding from the distal edge of the plunger member 1770 to engage the vertically protruding biased or tapered teeth 1780 formed on the proximal end of the rotationally driven indicator dial 1776. The angle or degree of the biased teeth 1780 causes a rotational force to be exerted by the vertically protruding actuating pegs 1782 on the biased teeth 1780, and in turn, the rotationally driven indicator dial 1776. As the plunger member 1770 is depressed, the rotationally driven indicator dial 1776 rotates transversely to the handle such that the numerical indicia 1778 that can be seen through the window 1774 formed in the body of the handle member body 1754 rotates to a second numerical indicia corresponding to the information about the distance advanced by the stylet's distal end from actuation of the plunger member 1770. In certain preferred embodiments, the numerical value displayed indicates the number of fiducials that have been deployed from the distal end of the needle.

When the plunger member 1770, which is movably disposed on the proximal end of the handle member 1754 and extends longitudinally through at least a portion of the handle lumen along or generally aligned with the handle's central longitudinal axis, is distally advanced through the handle lumen, the elongate collet 1762 and collar 1768, which is initially enclosed around the distal end of at least a portion of collet 1762, likewise advance distally through the handle lumen. Before initial actuation of the plunger member 1770, as depicted in FIG. 7B, at least a portion of the collar 1768 is contained within the distal end of the housing lumen of stopper housing 1766 and is engaged by the lower stopping lip of the stopper housing 1766. The collar 1768 is held taut around the distal end of the collet 1762 by the lower stopping lip of the stopper housing 1766, such that the collet jaws are compressed around or exert a clamping force on the stylet wire 1760.

As the user depresses the actuating plunger member 1770, as shown in FIG. 7C, the distal advancement of the collet 1762 causes the collar 1768 to exit the distal end of the stopper housing 1766 and advance distally generally aligned with the central longitudinal axis of the first handle member body 1754. The collet 1762, which is compressed tightly around the stylet 1760, grips the stylet 1760 and advances distally along with the collar 1768 and stylet 1760. As the collar 1768 advances generally aligned with the longitudinal axis of the first handle member body 1754, the collar 1768 reaches the buffer plate 1772. The collar 1768 engages the laterally protruding stopping lip of the buffer plate 1772, which prevents the collar 1768 from advancing and causes it to disengage from the collet 1762. The buffer lumen or hollowed out center, however, allows the collet 1762 to continue advancing distally generally aligned with the longitudinal axis of the first handle member body 1754 even after the collar 1768 has reached the laterally protruding stopping lip of the buffer plate 1772.

As the collet 1762 continues advancing distally, the collet 1762 advances distally from the distal end of the collar 1768, as shown in FIG. 7D. The collet 1762, being no longer compressed by the collar 1768, expands to relieve its grip on the stylet 1760. As the collar becomes less compressed around stylet 1760, the stylet 1760 is able to move independently of the collet 1762. By the time the collet 1762 has released its grip on the stylet 1760, stylet 1760 will have advanced distally generally aligned with the longitudinal axis of the first handle member body 1754 for a predetermined distance corresponding to the configuration and length of the plunger member 1770. The length and configuration of the plunger member 1770 limits the proximal/distal movement of the collet 1762, and in turn stylet 1760, and is dimensioned to correspond to the desired increment of stylet advancement. In some embodiments, a number of fiducials may be pre-loaded in the distal end of needle 1614, and the desired increment of stylet advancement corresponds to the length of advancement necessary to deploy, in a serial manner, one or some predetermined number of the pre-loaded fiducials 1790 from the distal end of the needle 1614, as shown in the exemplary embodiment of FIG. 7E. In one aspect, the mechanism may be considered as an alternative design for other incremental (e.g., one at a time, or "controlled plurality at a time") fiducial deployment systems where each actuation corresponding to a stylet advancement and/or change of exposed numerical indicia corresponds to deployment of a predetermined number of fiducials such as is shown, for example, in FIGS. 7A-7C of U.S. Pat. App. Pub. No. 2014/0243844 to Clancy et al., which is incorporated herein by reference in its entirety.

As the user or actuating device releases the plunger member 1770, the proximal-directed tendency or bias of the compression spring 1764 causes the plunger member 1770 to advance proximally as to return to fully pulled back position. As the plunger member 1770 is biased or urged to the proximal end of the first handle member body 1754, collet 1762 and collar 1768 likewise advance proximally towards the proximal end of the first handle member body 1754. As the collar 1768 reaches the lower stopping lip of the stopper housing 1766, the collar 1768 is prevented from advancing proximally any farther. The collet 1762 continues to advance proximally with the plunger member 1770 causing the distal end of the collet 1762 to retract into the distal end of the collar 1768. As the collet 1762 retracts into the collar 1768, the collar 1768 recompresses around collet 1762 and reestablishes a grip on the stylet 1760. As the plunger member 1770 returns to fully pulled back position, the collet 1762 and collar 1768 will have at least partially reentered the distal end of the stopper housing 1766 to come to rest against the laterally protruding lower stopping lip at the distal end of the housing lumen of stopper housing 1766, as shown in the embodiment of FIG. 7F.

As illustrated in the embodiment of FIG. 7G, depending on the configuration of sheath 1612 and the needle 1614, which in some embodiments may be attached to needle-attached handle member 1604 or in other embodiments to the handle component 1750, the stylet 1760 will have advanced distally sufficient distance towards the distal end of the needle 1614 to deploy the desired number of fiducials. In some configurations, the stylet will have advanced far enough to deploy one or more fiducials but may remain disposed at least partially within the needle 1614 and may have one or more additional fiducials disposed within needle 1614 awaiting deployment. In this scenario, subsequent numbers of fiducials may be deployed by additional, successive actuations of the plunger member 1770.

Those of skill in the art will appreciate with reference to the embodiments disclosed above that a predetermined number of fiducials may be released into a desired location by a single actuation of the lever, button, or other actuation member. The predetermined number preferably will be one, but may include a plurality of fiducials. The configuration of the present embodiments provide clear advantages over prior designs that utilize releasable end-plugs in a needle to retain fiducials, and/or that use less refined means of controlling the fiducial release than the notch/tab needle design and/or actuation handles described herein.

Drawings and particular features in the figures illustrating various embodiments are not necessarily to scale. Some drawings may have certain details magnified for emphasis, and any different numbers or proportions of parts should not be read as limiting, unless so-designated by one or more claims. Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. For example, a needle and fiducials of the present system may be used percutaneously, including in another minimally invasive surgical procedure, such as a laparoscopic-type procedure, within the scope of the claimed invention. For example, a target site may be a location in or near the gastrointestinal tract (e.g., liver, pancreas) such as those locations that may be accessible by endoscopy (using a minimally invasive endoscope introduced through a natural patient orifice, e.g., mouth, anus, vagina). This includes—more broadly—sites reachable through NOTES (natural orifice translumenal endoscopic surgery) procedures. The present method and device may also be used with other minimally-invasive surgical techniques such as percutaneous endoscopic procedures (e.g., laparoscopic procedures) or percutaneous non-endoscopic procedures, but most preferably is used with less invasive endoscopy procedures. It is therefore intended that the foregoing detailed description be regarded as illustrative rather than limiting. And, it should be understood that the following claims, including all equivalents, are intended to define the spirit and scope of this invention.

We claim:

1. A fiducial deployment system, said system comprising:
    a fiducial deployment needle retaining for distal deployment, in a controlled serial manner, a plurality of fiducials;
    a plunger driven collet handle configured for said fiducial needle deployment, the plunger driven collet handle comprising:
    an elongate handle member of the plunger driven collet handle, said elongate handle member defining a central longitudinal axis and an inner handle wall;
    a central collet member longitudinally movable in the elongate handle member, the collet member comprising:
    a distal end including collet jaws that surround and define a collet lumen, and
    a proximal end;
    a stylet disposed longitudinally through the deployment needle, extending proximally into the elongate handle member and through the collet lumen of the collet member;
    a collar member slidably engaged around the distal end of the collet member so that,
    in a first state, the stylet is releasably gripped by the collet jaws as the collet jaws are more constrainedly engaged by the collar member and that,
    in a second state wherein the collet jaws are less constrainedly engaged by the collar member, the collet is configured to slide proximally along the stylet; and
    a plunger actuation member extending distally into the elongate handle member and affixed to the proximal end of the central collet member, said plunger actuation member longitudinally movable within at least a portion of the elongate handle member in a manner configured to advance the collet member distally and to provide reciprocal proximal movement of the collet member with the plunger actuation member.

2. The system of claim 1, wherein the plunger actuation member is spring-urged proximally.

3. The system of claim 1, further comprising a stopper housing defining a housing lumen.

4. The system of claim 3, wherein the stopper housing further defines a lower stopping lip that effectively stops proximal movement of the collar member along the central longitudinal axis of the elongate handle member.

5. The system of claim 4, wherein in the first state the collar member constrains the collet member so as to exert a clamping force on the stylet when the plunger actuation member is at rest and the collet is engaged around the collar member.

6. The system of claim 3, further comprising a buffer plate disposed on the inner handle wall of the elongate handle member and defining at least one buffer stopping lip.

7. The system of claim 6, wherein the at least one buffer stopping lip is configured to effectively stop distal movement of the collar member along the central longitudinal axis of the elongate handle member while permitting continued distal movement of the collet member.

8. The system of claim 7, wherein—in the second state—the collar member is stopped by the at least one buffer stopping lip and is configured to circumferentially release the collet member, and thereby to diminish and/or remove clamping force of the collet member on the stylet when the collet member is advanced distally past the at least one buffer stopping lip.

9. The system of claim 1, further comprising an indicator dial disposed in the elongate handle member.

10. The system of claim 9, wherein the indicator dial includes indicia, viewable through a window in the elongate handle member, of the number of fiducials deployed by distalward movement of the collet member.

11. The system of claim 9, wherein the indicator dial is configured to be rotationally driven by distalward movement of the plunger actuation member.

12. The system of claim 11, wherein the plunger actuation member further defines one or more vertically protruding actuating members.

13. The system of claim 12 wherein the indicator dial further defines one or more vertically protruding biased teeth that engage the one or more vertically protruding actuating members of the plunger actuation member to rotationally drive the indicator dial.

14. A medical device handle configured for controlled incremental lengthwise stylet distal advancement through a cannula by repeated actuation, the handle comprising:
    an elongate outer handle body defining a longitudinal handle lumen;
    an elongate cannula attached directly or indirectly to a distal end of the handle body, the cannula defining a longitudinal cannula lumen in mechanical communication with the handle lumen;
    a collet disposed in the longitudinal handle lumen and longitudinally movable in the longitudinal handle lumen, wherein the collet is proximally spring-biased by a compression spring into a collar that circumferentially encompasses jaws of the collet and is configured to compress the jaws of the collet to releasably grip a stylet;
    the stylet extending distally through a longitudinal collet lumen of the collet into the longitudinal cannula lumen; and
    a plunger member disposed on the proximal end of the elongate outer handle body within the longitudinal handle lumen having a portion of the plunger member mechanically engaging the collet, configured such that a first actuation of the plunger member by moving it longitudinally relative to the longitudinal handle lumen is effective to move the collet and the stylet distally by a first predetermined increment and configured such that proximal, spring-biased reciprocation of the plunger and the collet provides for a second actuation of the plunger member by moving it longitudinally relative to the longitudinal handle lumen, wherein said second actuation of the plunger member is effective to move the collet and the stylet distally by a second predetermined increment.

15. The medical device handle of claim 14, wherein actuating of the plunger member by moving it transversely against, and/or longitudinally relative to the longitudinal handle lumen is effective to deploy one or more fiducials from a distal end of the elongate cannula.

16. The medical device handle of claim 14, configured such that repeated distalward actuation of the plunger and corresponding repeated movement of the collet distally, combined with proximal reciprocation of the collet in a state not grasping the stylet and not moving the stylet proximally, is effective to advance an incremental distal movement of the stylet longitudinally relative to the longitudinal handle lumen.

17. The medical device handle of claim 16, further comprising a stopper housing formed on an inner wall of the longitudinal handle lumen and configured effectively to prevent distal movement of the collar longitudinally relative to the longitudinal handle lumen.

18. The medical device handle of claim 17, wherein the stopper housing is configured effectively to disengage the collar from a distal end of the stylet and to allow distal movement of the collet relative to the stylet.

* * * * *